(12) United States Patent
Urade et al.

(10) Patent No.: US 8,765,750 B2
(45) Date of Patent: Jul. 1, 2014

(54) PIPERAZINE COMPOUND HAVING A PGDS INHIBITORY EFFECT

(75) Inventors: Yoshihiro Urade, Kyoto (JP); Makoto Kitade, Tsukuba (JP); Kazuhiko Shigeno, Tsukuba (JP); Keiko Yamane, Tsukuba (JP); Katsunao Tanaka, Tsukuba (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 14 days.

(21) Appl. No.: 13/522,605

(22) PCT Filed: Jan. 19, 2011

(86) PCT No.: PCT/JP2011/050840
§ 371 (c)(1),
(2), (4) Date: Jul. 17, 2012

(87) PCT Pub. No.: WO2011/090062
PCT Pub. Date: Jul. 28, 2011

(65) Prior Publication Data
US 2012/0309760 A1 Dec. 6, 2012

(30) Foreign Application Priority Data
Jan. 22, 2010 (JP) .................. 2010-012501

(51) Int. Cl.
| A61K 31/496 | (2006.01) |
| A61K 31/5377 | (2006.01) |
| C07D 401/14 | (2006.01) |
| C07D 413/14 | (2006.01) |
| C07D 403/14 | (2006.01) |

(52) U.S. Cl.
CPC ............ *C07D 403/14* (2013.01); *C07D 401/14* (2013.01); *A61K 31/496* (2013.01); *A61K 31/5377* (2013.01)
USPC .................. 514/235.8; 514/253.09; 544/121; 544/364

(58) Field of Classification Search
None
See application file for complete search history.

(56) References Cited

U.S. PATENT DOCUMENTS
2009/0281098 A1  11/2009  Urade

FOREIGN PATENT DOCUMENTS
| JP | 2004511553 A | 4/2004 |
| JP | 2004520435 A | 7/2004 |
| JP | 2008546784 A | 12/2008 |
| WO | 99/07672 A1 | 2/1999 |
| WO | 02/32893 A2 | 4/2002 |
| WO | 02/072570 A2 | 9/2002 |
| WO | 2007/001975 A1 | 1/2007 |
| WO | 2007/007778 A1 | 1/2007 |
| WO | 2007/041634 A1 | 4/2007 |
| WO | 2007/054623 A2 | 5/2007 |
| WO | 2008/108957 A2 | 9/2008 |
| WO | 2008/122787 A1 | 10/2008 |
| WO | 2009098282 A1 | 8/2009 |

OTHER PUBLICATIONS

Kajiwara et al. European Journal of Pharmacology vol. 667, pp. 389-395 (2011).*
Joo et al. Mediators of Inflammation vol. 2012, pp. 1-6 (2012).*
"Drug Combination may treat traumatic brain injury" from Science Daily provided by SUNY Downstate Medical Center, dated Sep. 18, 2010, retreived from the Internet at <www.sciencedaily.com/releases/2010/09/100917183029.htm> on Jan. 30, 2014.*
Buyse et al. European Heart Journal, vol. 30, pp. 116-124 (2009).*
Hardy et al., "The Bronchoconstrictor Effect of Inhaled Prostaglandin D2 in Normal and Asthmatic Men", The New England Journal of Medicine, vol. 311, No. 4, Jul. 26, 1984, pp. 209-213.
Hyo et al, "Expression of Prostaglandin D2 Synthase in Activated Eosinophils in Nasel Polyps", Arch. Otolaryngol. Head Neck Surg., vol. 133, No. 7, Jul. 2007, pp. 693-700.

(Continued)

*Primary Examiner* — Emily Bernhardt
(74) *Attorney, Agent, or Firm* — Rothwell, Figg, Ernst & Manbeck, P.C.

(57) ABSTRACT

The present invention provides a piperazine compound represented by Formula (I) or a salt thereof,

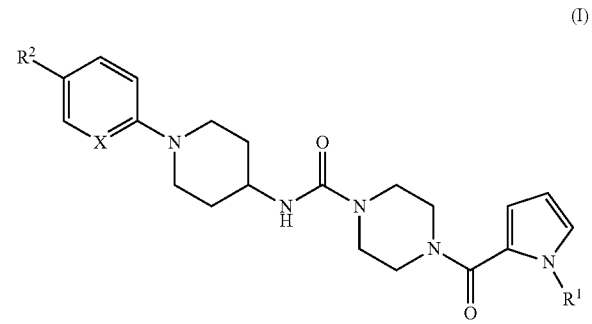

(I)

wherein
X represents CH or an N atom;
$R^1$ represents $C_{1-6}$ alkyl;
$R^2$ represents $C_{1-6}$ alkyl that may have one or more substituents, $C_{2-6}$ alkenyl that may have one or more substituents, —(C=O)—N($R^3$)($R^4$), or —(C=O)—$OR^5$,
$R^3$ and $R^4$ are the same or different, and each represents hydrogen or $C_{1-6}$ alkyl that may have one or more substituents; or $R^3$ and $R^4$, taken together with a nitrogen atom to which $R^3$ and $R^4$ are attached, may form a saturated heterocyclic group; and
$R^5$ represents hydrogen or $C_{1-6}$ alkyl that may have one or more substituents or aralkyl.

7 Claims, No Drawings

(56) References Cited

OTHER PUBLICATIONS

Lewis et al., "Prostaglandin D2 Generation After Activation of Rat and Human Mast Cells with ANTI-IgE", The Journal of Immunology, vol. 129, No. 4, Oct. 1982, pp. 1627-1631.

Murray et al., "Release of Prostaglandin D2 into Human Airways During Acute Antigen Challenge", The New England Journal of Medicine, vol. 315, No. 13, pp. 800-804, Sep. 25, 1986.

Okinaga et al, "Induction of hematopoietic prostaglandin D synthase in hyalinated necrotic muscle fibers: its implication in groupled necrosis", Acta. Neuropathol, 2002, vol. 104, pp. 377-384.

European Search Report dated May 31, 2013 for the corresponding EP Patent Application No. 11734668.4, 6 pgs.

Aritake, Kosuke, et al., "Structural and functional characterization of HQL-79, an orally selective inhibitor of human hematopoietic prostaglandin D synthase," Journal of Biological Chemistry, vol. 281, No. 22, pp. 15277-15288, 2006.

Hohwy, Morten, et al., "Novel prostaglandin D synthase inhibitors generated by fragment-based drug design," Journal of Medicinal Chemistry, vol. 51, pp. 2178-2186, 2008.

Inoue, Tsuyoshi, et al., "Mechanism of metal activation of human hematopoietic prostaglandin D synthase," Nature Structural Biology, vol. 10, No. 4, pp. 291-296, 2003.

Okinaga, Takeshi, et al., "Induction of hematopoietic prostaglandin D synthase in hyalinated necrotic muscle fibers: its implication in grouped necrosis", Acta Neuropathologica, vol. 104, Issue 4, pp. 377-384, 2002.

Thurairatnam, Sukanthini, "Hematopoietic prostaglandin D synthase inhibitors," Progress in Medicinal Chemistry, vol. 51, pp. 97-133, 2012.

Inoue, Tsuyoshi, et al., "Mechanism of metal activation of human hematopoietic prostaglandin D synthase," Nature Structural Biology, vol. 10, No. 5, p. 409, 2003. Corrigendum.

* cited by examiner

PIPERAZINE COMPOUND HAVING A PGDS INHIBITORY EFFECT

CROSS REFERENCE TO RELATED APPLICATION

This application is a 35 U.S.C. 371 National Phase Entry Application from PCT/JP2011/050840, filed Jan. 19, 2011, which claims the benefit of Japanese Patent Application No. 2010-012501 filed on Jan. 22, 2010, the disclosure of which is incorporated herein in its entirety by reference.

TECHNICAL FIELD

The present invention relates to a piperazine compound or a salt thereof, and a pharmaceutical composition containing the piperazine compound or salt thereof as an active ingredient, and in particular, to an agent for preventing and/or treating allergic disease and inflammatory disease due to its hematopoietic prostaglandin D synthase inhibiting action.

BACKGROUND ART

Prostaglandin D2 (PGD2) is the inflammatory mediator produced and released in the largest amounts by mast cells activated by the binding of antigens with immunoglobulin E (NPL 1), and is considered to play an important role in the elucidation of allergic reactions. PGD2 is detected at a high concentration in an asthmatic's bronchoalveolar fluid (NPL 2), and it was reported that bronchoconstriction was induced by PGD2 inhalation in asthmatic patients, but not in healthy subjects (NPL 3).

On the other hand, synthases that generate PGD2 are referred to as prostaglandin D synthases (PGDS). Two different types, hematopoietic prostaglandin D synthase and lipocalin-type prostaglandin D synthase, are known to exist. PGD2 participates in the onset and exacerbation of various diseases, including allergies, and in the regulatory mechanisms of the body; therefore, pharmaceutical preparations that can ameliorate excess production are considered to be very effective in the treatment of various diseases.

Human hematopoietic prostaglandin D synthases (H-PGDS) are mainly distributed throughout the placenta, lung, fetus liver, lymph node, brain, heart, thymus, bone marrow, and spleen. Moreover, at the cellular level, they are reported to be expressed in microglia in the brain, megakaryocyte, and Langerhans cells in the skin; Kupffer cells in the liver; macrophages; and many antigen-presenting cells such as dendritic cells, mast cells, and Th2 cells.

From the fact that H-PGDS are highly expressed in mast cells or inflammatory cells at nasal mucosa in allergic rhinitis, or nasal polyps in chronic sinusitis, it is thought that PGD2 produced by H-PGDS plays an important role in the onset and exacerbation of allergic diseases, such as asthma, rhinosinusitis, dermatitis, and chronic obstructive pulmonary disease (NPL4). Further, the expression of H-PGDS is confirmed in the necrosed part of skeletal muscle, in which the expression of H-PGDS does not generally occur (NPL5). For this reason, it is suggested that PGD2 produced by a hematopoietic prostaglandin D synthase participates in diseases accompanied by tissue damage, such as muscular dystrophy, amyotrophic lateral sclerosis, multiple sclerosis, ulcerative colitis, rheumatoid arthritis, and chronic obstructive arterial disease.

Therefore, an H-PGDS inhibitor is expected to find application as a pharmaceutical preparation that is useful as an agent for preventing and/or treating diseases in which PGD2 produced by a hematopoietic prostaglandin D synthase or a metabolite thereof participates, such as allergic disease, inflammatory disease, muscle necrosis, and traumatic brain injury.

There are some reports on an H-PGDS inhibitor (for example, PTL 1 and 2), and Patent Literature 3 discloses an H-PGDS inhibitor having a structure similar to that of the compound of the present invention. In addition, piperazine compounds have been widely studied as useful pharmacological agents in addition to H-PGDS inhibitors.

Patent Literature 4 discloses, as a hedgehog signaling inhibitor, a piperazine compound having a furyl carbonyl piperazine structure.

Patent Literature 5 (WO99/007672) discloses a wide range of piperazine compounds as compounds that interact with potassium channels.

CITATION LIST

Patent Literature

PTL 1: WO2007-007778
PTL 2: WO2007-041634
PTL 3: WO2008-122787
PTL 4: WO2007-054623
PTL 5: WO99/007672

Non-Patent Literature

NPL 1: J. Immunol., 129, 1627-1631 (1982)
NPL 2: N. Eng. J. Med., 315, 800-804 (1986)
NPL 3: N. Eng. J. Med., 311, 209-213 (1984)
NPL 4: Arch. Otolaryngol Head Neck Surg., 133, 693-700 (2007)
NPL 5: Acta Neuropathol., 104, 377-384 (2002)

SUMMARY OF INVENTION

Technical Problem

The primary object of the present invention is to provide a novel compound that exhibits, at a low dose, a high inhibitory effect on prostaglandin D synthases; and, in particular, on H-PGDS.

Another ancillary object of the present invention is to provide a medicine with few side effects and high safety, the medicine being effective, due to its H-PGDS inhibiting action, in preventing and/or treating diseases mediated by PGD2 generated by the synthase or metabolite thereof.

Solution to Problem

The present inventors conducted extensive research on compounds having an H-PGDS inhibiting action, and found that a novel piperazine compound represented by Formula (I) has an extremely excellent inhibiting action on H-PGDS. The inventors conducted further research, and have accomplished the present invention.

The present invention provides a piperazine compound, a pharmaceutical composition, a prostaglandin D synthase inhibitor, and an agent for preventing or treating a disease associated with prostaglandin D2 or a metabolite thereof, as described below.

Item 1.

A piperazine compound represented by Formula (I) or a salt thereof,

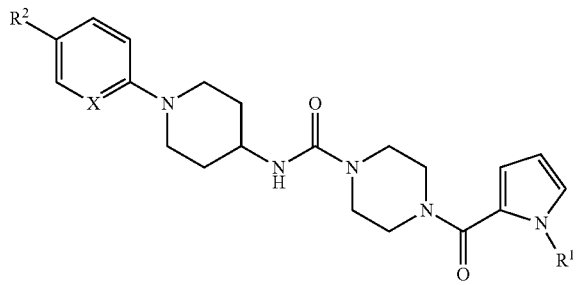

wherein

X represents CH or an N atom;

$R^1$ represents $C_{1-6}$ alkyl;

$R^2$ represents $C_{1-6}$ alkyl that may have one or more substituents, $C_{2-6}$ alkenyl that may have one or more substituents, —(C=O)—N($R^3$)($R^4$), or —(C=O)—$OR^5$, $R^3$ and $R^4$ are the same or different, and each represents hydrogen or $C_{1-6}$ alkyl that may have one or more substituents; or $R^3$ and $R^4$, taken together with a nitrogen atom to which $R^3$ and $R^4$ are attached, may form a saturated heterocyclic group; and $R^5$ represents hydrogen or $C_{1-6}$ alkyl that may have one or more substituents or aralkyl.

Item 2.

The piperazine compound according to Item 1 or a salt thereof, wherein

X represents CH or an N atom;

$R^1$ represents methyl or ethyl;

$R^2$ represents $C_{1-3}$ alkyl that may have one or more carbamoyl or unsaturated heterocyclic groups as substituents, propenyl that may have one or more carbamoyl groups as substituents, —(C=O)—N($R^3$)($R^4$), or —(C=O)—$OR^5$;

one of $R^3$ and $R^4$ represents hydrogen and the other represents $C_{1-6}$ alkyl that may have one or more saturated or unsaturated heterocyclic groups as substituents; or $R^3$ and $R^4$, taken together with a nitrogen atom to which $R^3$ and $R^4$ are attached, may form pyrrolidinyl, piperidinyl, piperazinyl, and morpholino; and $R^5$ represents hydrogen, methyl, ethyl, tert-butyl, or benzyl.

Item 3.

The piperazine compound according to Item 1 or 2 or a salt thereof, wherein

X represents CH or an N atom;

$R^1$ represents methyl;

$R^2$ represents $C_{1-3}$ alkyl that may have any one of morpholinocarbamoyl and triazolyl groups as a substituent, —(C=O)—N($R^3$)($R^4$), or —(C=O)—$OR^5$; and the triazolyl may have one or two $C_{1-6}$ alkyl as substituents;

one of $R^3$ and $R^4$ represents hydrogen and the other represents $C_{1-3}$ alkyl that may have one or more morpholino or pyridyl groups as substituents; or $R^3$ and $R^4$, taken together with a nitrogen atom to which $R^3$ and $R^4$ are attached, may form morpholino; and $R^5$ represents hydrogen.

Item 4.

The piperazine compound according to any one of Items 1 to 3 or a salt thereof, wherein X represents CH;

$R^1$ represents methyl;

$R^2$ represents linear $C_{1-3}$ alkyl that may have any one of 1,2,3-triazolyl, 1,2,4-triazolyl, and 3,5-dimethyl-1,2,4-triazolyl as a substituent, —(C=O)—N($R^3$)($R^4$), or —(C=O)—$OR^5$;

$R^3$ and $R^4$, taken together with a nitrogen atom to which $R^3$ and $R^4$ are attached, may form morpholino; and $R^5$ represents hydrogen.

Item 5.

The piperazine compound according to Item 1 or salt thereof selected from the group consisting of:

4-(4-(4-((1-methylpyrrol-2-yl)-carbonyl)-1-piperazinecarbamoyl)piperidin-1-yl)-benzoic acid, 4-((1-methylpyrrol-2-yl)-carbonyl)-N-(1-(4-(pyridin-3-ylmethylcarbamoyl)phenyl)-piperidin-4-yl)-1-piperazinecarboxamide, 4-((1-methylpyrrol-2-yl)-carbonyl)-N-(1-(4-(2-morpholinoethylcarbamoyl)-phenyl)-piperidin-4-yl)-1-piperazinecarboxamide, 4-((1-methylpyrrol-2-yl)-carbonyl)-N-(1-(4-(4-morpholinylcarbonyl)phenyl)-piperidin-4-yl)-1-piperazinecarboxamide, 4-((1-methylpyrrol-2-yl)-carbonyl)-N-(1-(4-(1-piperidinylcarbonyl)phenyl)-piperidin-4-yl)-1-piperazinecarboxamide, 4-((1-methylpyrrol-2-yl)-carbonyl)-N-(1-(4-(1-pyrrolidinylcarbonyl)phenyl)-piperidin-4-yl)-1-piperazinecarboxamide, 4-((1-methylpyrrol-2-yl)-carbonyl)-N-(1-(4-(2-(1,2,3-triazol-1-yl)-ethyl)-phenyl)-piperidin-4-yl)-1-piperazinecarboxamide, 4-((1-methylpyrrol-2-yl)-carbonyl)-N-(1-(4-(3-(1,2,4-triazol-1-yl)-propyl)-phenyl)-piperidin-4-yl)-1-piperazinecarboxamide, 4-((1-methylpyrrol-2-yl)-carbonyl)-N-(1-(4-(3-(3,5-dimethyl-1,2,4-triazol-1-yl)-propyl)-phenyl)-piperidin-4-yl)-1-piperazinecarboxamide, 4-((1-methylpyrrol-2-yl)-carbonyl)-N-(1-(4-(3-(1,2,3-triazol-1-yl)-propyl)-phenyl)-piperidin-4-yl)-1-piperazinecarboxamide, 4-((1-methylpyrrol-2-yl)-carbonyl)-N-(1-(4-(3-morpholino-3-oxopropen-1-yl)-phenyl)-piperidin-4-yl)-1-piperazinecarboxamide, 4-((1-methylpyrrol-2-yl)-carbonyl)-N-(1-(4-(3-morpholino-3-oxopropyl)-phenyl)-piperidin-4-yl)-1-piperazinecarboxamide, 6-(4-(4-((1-methylpyrrol-2-yl)-carbonyl)-1-piperazinecarbamoyl)-piperidin-1-yl)-nicotinic acid, 4-((1-methylpyrrol-2-yl)-carbonyl)-N-(1-(5-(4-morpholinylcarbonyl)pyridin-2-yl)-piperidin-4-yl)-1-piperazinecarboxamide, 4-((1-ethylpyrrol-2-yl)-carbonyl)-N-(1-(4-(2-morpholinoethylcarbamoyl)phenyl)-piperidin-4-yl)-1-piperazinecarboxamide, and 4-((1-ethylpyrrol-2-yl)-carbonyl)-N-(1-(4-(2-(1,2,3-triazol-1-yl)-ethyl)-phenyl)-piperidin-4-yl)-1-piperazinecarboxamide.

Item 6.

A pharmaceutical composition comprising an effective amount of at least one of the compounds according to Items 1 to 5 or pharmaceutically acceptable salts thereof, and a pharmaceutically acceptable carrier.

Item 7.

A prostaglandin D synthase inhibitor comprising an effective amount of a compound according to any one of Items 1 to 5 or a pharmaceutically acceptable salt thereof, and a pharmaceutically acceptable carrier.

Item 8.

An agent for preventing or treating a disease associated with prostaglandin D2 or a metabolite thereof, the agent comprising an effective amount of a compound according to any one of Items 1 to 5 or a pharmaceutically acceptable salt thereof, and a pharmaceutically acceptable carrier.

Item 9.

The agent according to Item 8, wherein the disease associated with prostaglandin D2 or a metabolite is an allergic disease or inflammatory disease.

Item 10.

A method for treating a disease associated with prostaglandin D2 or a metabolite thereof, comprising administering to a patient in need of such treatment an effective amount of a piperazine compound represented by Formula (I) or a salt thereof

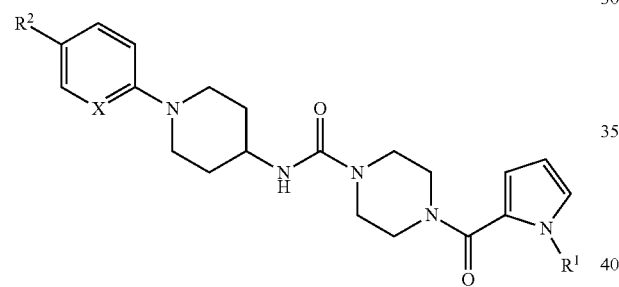

wherein

X represents CH or an N atom;

$R^1$ represents $C_{1-6}$ alkyl;

$R^2$ represents $C_{1-6}$ alkyl that may have one or more substituents, $C_{2-6}$ alkenyl that may have one or more substituents, —(C=O)—N($R^3$)($R^4$), or —(C=O)—$OR^5$, $R^3$ and $R^4$ are the same or different, and each represents hydrogen or $C_{1-6}$ alkyl that may have one or more substituents; or $R^3$ and $R^4$ taken together with a nitrogen atom to which $R^3$ and $R^4$ are attached, may form a saturated heterocyclic group; and $R^5$ represents hydrogen or $C_{1-6}$ alkyl that may have one or more substituents or aralkyl.

Item 11.

The method according to Item 10, wherein the disease associated with prostaglandin D2 or a metabolite thereof is an allergic disease or inflammatory disease.

Item 12.

A piperazine compound represented by Formula I or a salt thereof for use in the treatment of a disease associated with prostaglandin D2 or a metabolite thereof

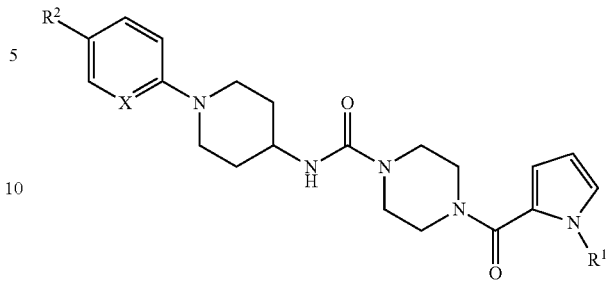

wherein

X represents CH or an N atom;

$R^1$ represents $C_{1-6}$ alkyl;

$R^2$ represents $C_{1-6}$ alkyl that may have one or more substituents, $C_{2-6}$ alkenyl that may have one or more substituents, —(C=O)—N($R^3$)($R^4$), or —(C=O)—$OR^5$, $R^3$ and $R^4$ are the same or different, and each represents hydrogen or $C_{1-6}$ alkyl that may have one or more substituents; or $R^3$ and $R^4$ taken together with a nitrogen atom to which $R^3$ and $R^4$ are attached, may form a saturated heterocyclic group; and $R^5$ represents hydrogen or $C_{1-6}$ alkyl that may have one or more substituents or aralkyl.

Item 13.

Use of a piperazine compound represented by Formula I or a salt thereof for treating a disease associated with prostaglandin D2 or a metabolite thereof

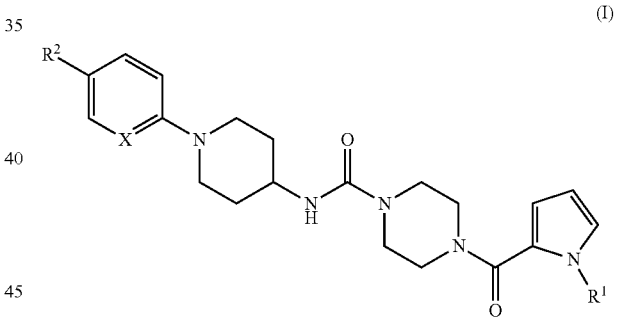

wherein

X represents CH or an N atom;

$R^1$ represents $C_{1-6}$ alkyl;

$R^2$ represents $C_{1-6}$ alkyl that may have one or more substituents, $C_{2-6}$ alkenyl that may have one or more substituents, —(C=O)—N($R^3$)($R^4$), or —(C=O)—$OR^5$, $R^3$ and $R^4$ are the same or different, and each represents hydrogen or $C_{1-6}$ alkyl that may have one or more substituents; or $R^3$ and $R^4$ taken together with a nitrogen atom to which $R^3$ and $R^4$ are attached, may form a saturated heterocyclic group; and $R^5$ represents hydrogen or $C_{1-6}$ alkyl that may have one or more substituents or aralkyl.

Advantageous Effects of Invention

The present invention provides a novel piperazine compound represented by the above Formula (I) or a salt thereof, which is useful as a prostaglandin D synthase inhibitor; and, in particular, as an H-PGDS inhibitor.

The piperazine compound or a salt thereof according to the present invention has excellent H-PGDS inhibitory activity in vitro. Further, it is revealed that the piperazine compound or a salt thereof exhibits PGD2 production inhibiting action in a nasal cavity washing liquid in guinea pigs with antigen-induced rhinitis, and that the piperazine compound or a salt thereof has an excellent nasal congestion improving action.

Thus, based on its excellent H-PGDS inhibitory activity, the piperazine compound or a salt thereof according to the present invention is useful as an agent for preventing and/or treating a disease associated with PGD2 or a metabolite thereof, such as an allergic disease and inflammatory disease, and is expected to have other useful effects.

DESCRIPTION OF EMBODIMENTS

The piperazine compound of the present invention is a piperazine compound represented by Formula (I) or a salt thereof,

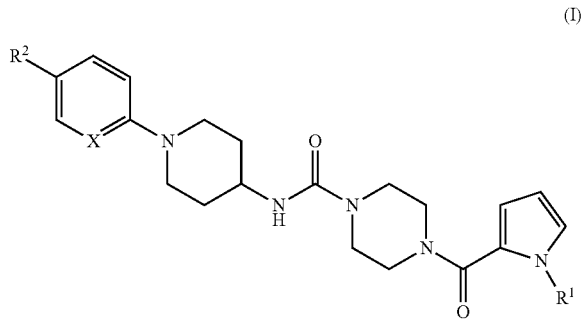

(I)

wherein
X represents CH or an N atom;
$R^1$ represents $C_{1-6}$ alkyl;
$R^2$ represents $C_{1-6}$ alkyl that may have one or more substituents, $C_{2-6}$ alkenyl that may have one or more substituents, —(C=O)—N($R^3$)($R^4$), or —(C=O)—$OR^5$;
$R^3$ and $R^4$ are the same or different, and each represents hydrogen or $C_{1-6}$ alkyl that may have one or more substituents; or $R^3$ and $R^4$, taken together with a nitrogen atom to which $R^3$ and $R^4$ are attached, may form a saturated heterocyclic group; and
$R^5$ represents hydrogen or $C_{1-6}$ alkyl that may have one or more substituents or aralkyl.

The piperazine compound of the present invention, which is represented by Formula (I), is a compound having both (N-alkylpyrrol-2-yl)carbonyl and (piperidin-4-yl)aminocarbonyl, and is a novel compound not specifically disclosed in the aforementioned literature.

For example, Patent Literature 3 (WO2008/122787) discloses a wide range of piperazine compounds that inhibit H-PGDS; however, Patent Literature 3 is different from the present invention in that the compound of the present invention has (piperidin-4-yl)aminocarbonyl. In addition, Patent Literature 3 is completely silent about a piperazine compound having (N-alkylpyrrol-2-yl)carbonyl, which is contained in the compound of the present invention. Further, as shown in the Test Examples described below, the compounds demonstrated in the Examples (Reference Examples 12 to 17) of Patent Literature 3 do not exhibit PGD2 production inhibiting action in a nasal cavity washing liquid in guinea pigs with antigen-induced rhinitis.

Patent Literature 4 (WO2007/054623) discloses as an inhibitor of hedgehog signaling a piperazine compound having a furyl carbonyl piperazine structure; however, Patent Literature 4 is different from the present invention in that (N-alkylpyrrol-2-yl)carbonyl used in the compound of the present invention is limited to furyl carbonyl. Further, Patent Literature 4 is completely silent about H-PGDS inhibiting action.

Patent Literature 5 (WO99/007672) discloses a furyl carbonyl piperazine compound, a benzoylpiperazine compound, etc., as a compound that interacts with a potassium channel. However, Patent Literature 5 does not disclose a compound having (N-alkylpyrrol-2-yl)carbonyl as in the present compound, and is completely silent about H-PGDS inhibiting action.

As shown in the Test Examples below, a piperazine compound having no (N-alkylpyrrol-2-yl)carbonyl exhibits almost no H-PGDS inhibiting action.

Examples of "substituents" in the present specification include halogen, hydroxyl, cyano, nitro, alkyl, halogenoalkyl, cycloalkyl, cycloalkyl-alkyl, aralkyl, alkenyl, alkynyl, alkoxy, halogenoalkoxy, cycloalkoxy, cycloalkyl-alkoxy, aralkyloxy, alkylthio, cycloalkyl-alkylthio, amino, mono- or di-alkylamino, cycloalkyl-alkylamino, acyl, acyloxy, oxo, carboxyl, alkoxycarbonyl, aralkyloxycarbonyl, carbamoyl, saturated or unsaturated heterocyclic groups, aromatic hydrocarbon, saturated heterocycloxy group, etc. When such a substituent is present, the number thereof is typically 1, 2, or 3.

In the substituents, examples of halogen include chlorine, bromine, fluorine, and iodine.

In the substituents, alkyl or halogenoalkyl is preferably a straight or branched $C_{1-6}$ or $C_{1-4}$alkyl group or a group in which one to all of the hydrogen atoms of the alkyl group is substituted with halogen described above. Examples thereof include alkyl groups such as methyl, ethyl, n-propyl, isopropyl, n-butyl, isobutyl, sec-butyl, tert-butyl, pentyl, and hexyl; and halogenoalkyl groups such as trifluoromethyl.

In the substituents, cycloalkyl is preferably a $C_{3-7}$ cycloalkyl group, and examples thereof include cyclopropyl, cyclobutyl, cyclopentyl, cyclohexyl, and cycloheptyl.

In the substituents, cycloalkyl-alkyl is preferably a $C_{1-6}$ alkyl group substituted with a $C_{3-7}$ cycloalkyl group, and examples thereof include cyclopropylmethyl, cyclopropylethyl, cyclobutylmethyl, cyclopentylmethyl, and cyclohexylmethyl.

In the substituents, aralkyl is preferably a straight or branched $C_{1-6}$ alkyl group substituted with a $C_{6-14}$ aromatic hydrocarbon group, and examples thereof include benzyl, phenylethyl, phenylpropyl, naphthylmethyl, and naphthylethyl.

In the substituents, alkenyl is preferably a $C_{2-6}$ alkenyl group containing a carbon-carbon double bond, and examples thereof include vinyl, allyl, methylvinyl, propenyl, butenyl, pentenyl, and hexenyl.

In the substituents, alkynyl is preferably a $C_{2-6}$ alkynyl group containing a carbon-carbon triple bond, and examples thereof include ethynyl and propargyl.

In the substituents, alkoxy or halogenoalkoxy is preferably a straight or branched $C_{1-6}$ alkoxy group or the alkoxy group substituted with halogen described above, and examples thereof include methoxy, ethoxy, n-propoxy, isopropoxy, 1-methylpropoxy, n-butoxy, isobutoxy, tert-butoxy, 2-methylbutoxy, neopentyloxy, pentan-2-yloxy, fluoromethoxy, difluoromethoxy, trifluoromethoxy, 1,1-difluoroethoxy, 2,2-difluoroethoxy, 2,2,2-trifluoroethoxy, 1,1,2,2-tetrafluoroethoxy, perfluoroethoxy, 3-fluoro-2-

(fluoromethyl)-propoxy, 1,3-difluoropropan-2-yloxy, and 2,2,3,3,3-pentafluoro-1-propoxy.

In the substituents, cycloalkoxy is preferably a $C_{2-7}$ cycloalkoxy group, and examples thereof include cyclopropoxy, cyclobutoxy, cyclopenthyloxy, cyclohexyloxy, and cycloheptyloxy.

In the substituents, cycloalkyl-alkoxy is preferably a $C_{1-6}$ alkoxy group substituted with a $C_{3-7}$ cycloalkyl group, and examples thereof include cyclopropylmethoxy, cyclopropylethoxy, cyclobutylmethoxy, cyclopentylmethoxy, and cyclohexylmethoxy.

In the substituents, aralkyloxy is preferably an oxy group having the aforementioned aralkyl group, and examples thereof include benzyloxy, phenethyloxy, phenylpropyloxy, naphthylmethyloxy, and naphthylethyloxy.

In the substituents, alkylthio is preferably a straight or branched $C_{1-6}$ alkylthio group, and examples thereof include methylthio, ethylthio, n-propylthio, isopropylthio, n-butylthio, isobutylthio, sec-butylthio, tert-butylthio, pentylthio, and hexylthio.

In the substituents, cycloalkyl-alkylthio is preferably a $C_{1-6}$ alkylthio group substituted with a $C_{3-7}$ cycloalkyl group, and examples thereof include cyclopropylmethylthio, cyclopropylethylthio, cyclobutylmethylthio, cyclopentylmethylthio, and cyclohexylmethylthio.

In the substituents, mono- or di-alkylamino is an amino group mono- or di-substituted with the aforementioned straight or branched $C_{1-6}$ alkyl group, and examples thereof include methylamino, dimethylamino, ethylamino, diethylamino, and methylethylamino.

In the substituents, cycloalkyl-alkylamino is an alkylamino group substituted with the aforementioned cycloalkyl group, and examples thereof include cyclopropylmethylamino, cyclobutylmethylamino, and cyclopentylmethylamino.

In the substituents, acyl is a straight or branched $C_{1-6}$ acyl group or benzoyl group, and examples thereof include formyl, acetyl, propionyl, n-butyryl, isobutyryl, valeryl, isovaleryl, and pivaloyl.

In the substituents, acyloxy is a straight or branched $C_{1-6}$ alkanoyloxy group or benzoyloxy group, and examples thereof include formyloxy, acetoxy, propionyloxy, n-butyryloxy, isobutyryloxy, valeryloxy, isovaleryloxy, and pivaloyloxy.

In the substituents, alkoxycarbonyl is a carbonyl group substituted with the aforementioned alkoxy group, and examples thereof include methoxycarbonyl, ethoxycarbonyl, n-propoxycarbonyl, isopropoxycarbonyl, 1-methylpropoxycarbonyl, n-butoxycarbonyl, isobutoxycarbonyl, tert-butoxycarbonyl, 2-methyl-butoxycarbonyl, neopentyloxycarbonyl, and pentan-2-yloxycarbonyl.

In the substituents, aralkyloxycarbonyl is preferably a carbonyl group substituted with the aforementioned aralkyloxy group, and examples thereof include benzyloxycarbonyl, phenethyloxycarbonyl, phenylpropyloxycarbonyl, naphthlmethyloxycarbonyl, and naphthylethyloxycarbonyl.

In the substituents, examples of carbamoyl include —$CONH_2$, (mono- or di-alkyl)carbamoyl, (mono- or di-aryl) carbamoyl, (N-alkyl-N-aryl) carbamoyl, pyrrolidinocarbamoyl, piperidinocarbamoyl, piperazinocarbamoyl, and morpholinocarbamoyl.

In the substituents, saturated or unsaturated heterocyclic groups are preferably monocyclic or bicyclic saturated or unsaturated heterocyclic groups that may have any one of oxygen, nitrogen, or sulfur, preferably in an amount of 1 to 4. Examples thereof include pyrrolidinyl, piperidinyl, piperazinyl, hexamethyleneimino, morpholino, thiomorpholino, homopiperazinyl, tetrahydrofuranyl, tetrahydropyranyl, imidazolyl, thienyl, furyl, pyrrolyl, oxazolyl, isoxazolyl, triazolyl, isothiazolyl, pyrazolyl, triazolyl, tetrazolyl, pyridyl, pyrazyl, pyrimidinyl, pyridazinyl, indolyl, isoindolyl, indazolyl, methylenedioxyphenyl, ethylenedioxyphenyl, benzofuranyl, dihydrobenzofuranyl, benzoimidazolyl, benzoxazolyl, benzothiazolyl, purinyl, quinolyl, isoquinolyl, quinazolinyl, and quinoxalyl.

In the substituents, aromatic hydrocarbon is preferably a $C_{6-14}$ aromatic hydrocarbon group, and examples thereof include phenyl and naphthyl. In the substituents, saturated heterocycloxy group is a monocyclic saturated heterocyclic group having any one of oxygen, nitrogen, and sulfur in an amount of one or two, and examples thereof include oxy groups having pyrrolidinyl, piperidinyl, piperazinyl, hexamethyleneimino, morpholino, thiomorpholino, homopiperazinyl, tetrahydrofuranyl, tetrahydropyranyl, etc., such as tetrahydrofuranyloxy and tetrahydropyranyloxy.

"$C_{1-6}$ alkyl" represented by $R^1$ in Formula (I) is a straight or branched $C_{1-6}$ alkyl group, and examples thereof include methyl, ethyl, n-propyl, isopropyl, n-butyl, isobutyl, tert-butyl, n-pentyl, and n-hexyl. Of these, methyl and ethyl are preferable, and methyl is more preferable.

Examples of the "$C_{1-6}$ alkyl" of the "$C_{1-6}$ alkyl that may have one or more substituents" represented by $R^2$ in Formula (I) include $C_{1-6}$ alkyl represented by $R^1$. Of these, $C_{1-3}$ alkyl is preferable, and straight $C_{1-3}$ alkyl such as methyl, ethyl, and n-propyl are more preferable.

Examples of the "substituents" of the "$C_{1-6}$ alkyl that may have one or more substituents" represented by $R^2$ include the above-mentioned substituents. Carbamoyl or unsaturated heterocyclic groups are preferable; morpholinocarbamoyl and triazolyl are more preferable; and morpholinocarbamoyl, 1,2,3-triazolyl, and 1,2,4-triazolyl are particularly preferable. The unsubstituted heterocyclic groups may have substituents. A preferable substituent is methyl, and the number of substituents is 1 or 2.

Particularly preferable examples of "$C_{1-6}$ alkyl that may have one or more substituents" represented by $R^2$ include morpholinocarbamoyl-ethyl, 1,2,3-triazolyl-ethyl, 1,2,3-triazolyl-propyl, 1,2,4-triazolyl-propyl, 3,5-dimethyl-1,2,4-triazolyl-ethyl, and 3,5-dimethyl-1,2,4-triazolyl-propyl.

Examples of the "$C_{2-6}$ alkenyl" of the "$C_{2-6}$ alkenyl that may have one or more substituents" represented by $R^2$ include $C_{2-6}$ alkenyl described above. Of these, vinyl is preferable.

Examples of the "substituents" of the "$C_{2-6}$ alkenyl that may have one or more substituents" represented by $R^2$ include the above-mentioned substituents. Carbamoyl that may have one or more substituents is preferable; and morpholinocarbamoyl is more preferable.

Examples of the "$C_{1-6}$ alkyl" of the "$C_{1-6}$ alkyl that may have one or more substituents" represented by $R^3$ and $R^4$ in Formula (I) include $C_{1-6}$ alkyl represented by $R^1$. Of these, $C_{1-3}$ alkyl is preferable; and methyl or ethyl is more preferable.

Examples of the "substituents" of the "$C_{1-6}$ alkyl that may have one or more substituents" represented by $R^3$ and $R^4$ include the above-mentioned substituents. Of these, saturated or unsaturated heterocyclic groups are preferable; morpholino or pyridyl is more preferable.

It is preferred that one of $R^3$ and $R^4$ is hydrogen and the other is $C_{1-6}$ alkyl that may have one or more substituents; it is particularly preferred that one of $R^3$ and $R^4$ is hydrogen and the other is $C_{1-3}$ alkyl that has morpholino or pyridyl.

Examples of the "saturated heterocyclic group" that may be formed by $R^3$ and $R^4$ in Formula (I) together with a nitrogen atom to which $R^3$ and $R^4$ are attached, include pyrrolidinyl, piperidinyl, piperazinyl, and morpholino; and pyrrolidinyl, piperidinyl, and morpholino are preferable.

Preferable examples of the "$C_{1-6}$ alkyl that may have one or more substituents" represented by $R^5$ in Formula (I) include methyl, ethyl, tert-butyl, and benzyl. $R^5$ is preferably hydrogen.

The piperazine compound of the present invention can be produced according to the following Reaction Schemes 1 to 7.

Method for Producing the Compound of the Present Invention

A representative method for producing the compound represented by Formula (I) is described.

[Method 1]

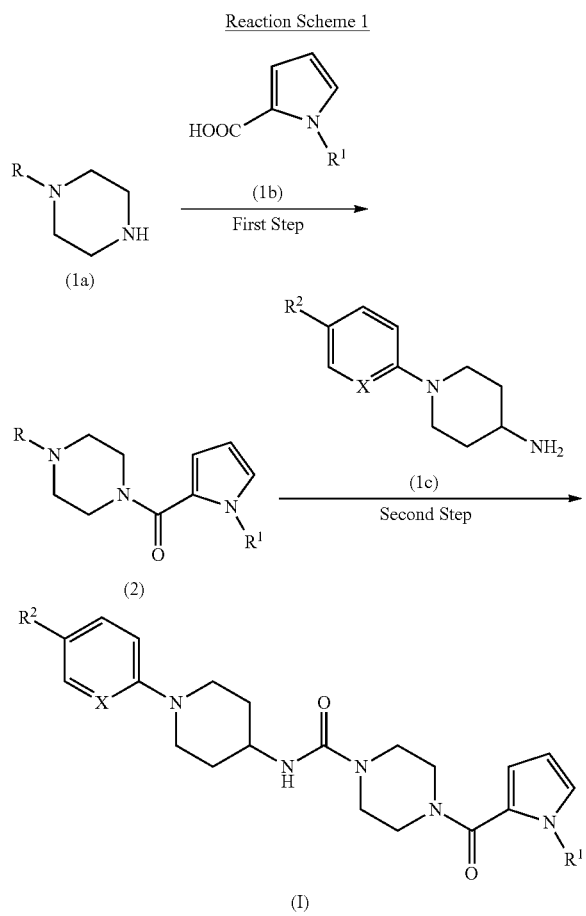

Reaction Scheme 1

In the above Reaction Scheme 1, X, $R^1$ and $R^2$ are the same as above, and R represents a protective group of amino group or hydrogen.

First Step

The amide compound shown in Formula (2) can be obtained by condensing the piperazine compound shown in Formula (1a) or a salt thereof with the pyrrolecarboxylic acid compound shown in Formula (1b) or an active species thereof by an ordinary method.

Examples of the active species of compound (1b) include ordinary esters such as methyl esters; acid halides such as acid chlorides; active esters with N-hydroxybenzotriazole, etc.; symmetrical acid anhydrides; and mixed acid anhydrides with alkyl carbonic acids, etc.

When the compound (1b) is reacted with a free acid, or when an active ester or acid halide is reacted without being isolated, a condensation agent such as 1-ethyl-3-(3-dimethylamino propyl)carbodiimide hydrochloride and 4-(4,6-dimethoxy-1,3,5-triazin-2-yl)-4-methylmorpholinium chloride is preferably used.

When 0.5 to 10 moles, and preferably 0.8 to 2 moles of the carboxylic acid compound shown in Formula (1b) or an active species thereof is used relative to 1 mole of the piperazine compound shown in Formula (1a) or a salt thereof, the amount of the condensation agent is 0.5 to 20 moles, and preferably 0.8 to 3 moles relative to 1 mole of the piperazine compound shown in Formula (1a) or a salt thereof.

Although dependent on the active species or condensation agent used, the reaction is normally carried out in a solvent which is inactive to the reaction at −20 to 150° C., and preferably at 0 to 100° C. Examples of such a solvent include halogenated hydrocarbons such as dichloromethane and chloroform; aromatic hydrocarbons such as toluene; ethers such as tetrahydrofuran; esters such as ethyl acetate; alcohols such as methanol and ethanol; water; acetonitrile; N,N-dimethylformamide; N,N-dimethylacetamide; dimethylsulfoxide; and pyridine. The reaction time is about 1 to 24 hours.

The reaction may proceed smoothly if it is carried out in the presence of 0.5 to 20 moles, and preferably 0.8 to 5 moles of a base such as triethylamine, diisopropylethylamine, N-methylmorpholine, N,N-dimethylaniline, 4-(N,N-dimethylamino)pyridine, and pyridine, relative to 1 mole of the piperazine compound shown in Formula (1a) or a salt thereof.

Second Step

In the second step, the protective group R of amino group in the amide compound shown in Formula (2) is deprotected by an ordinary, known method, and the result and the amine compound shown in Formula (1c) or an active species thereof are condensed by an ordinary method to obtain the compound shown in Formula (I).

Deprotection can be carried out under acidic conditions when the protective group R is formyl, tert-butoxycarbonyl, or the like; and deprotection can be performed by, for example, a catalytic reduction method when the protective group R is benzyl, benzyloxycarbonyl, or the like.

In the condensation, it is preferable to use an active species having a leaving group that is prepared by reacting the amine compound shown in Formula (1c) or a salt thereof with triphosgene, 1,1'-carbonyldiimidazole (CDI), phenyl chloroformate, 4-nitrophenyl chloroformate, ethyl chloroformate, or the like, in a solvent that is inactive to the reaction, such as dichloromethane, chloroform, tetrahydrofuran, acetonitrile, ethyl acetate, or N,N-dimethylacetamide, at −50 to 150° C., and preferably −20 to 100° C., in the presence or absence of an organic base such as triethylamine or pyridine. The reaction time is about 1 to 24 hours.

The active species of Formula (1c) may have a leaving group. The active species may be used for reaction after isolation, or may be prepared in a reaction system and used without isolation. Examples of the leaving group include chlorine, imidazolyl, phenoxy, nitrophenoxy, and ethoxy.

Examples of the salts of the amine compound shown in Formula (2) include acid addition salts with inorganic acids, such as hydrochloric acid, hydrobromic acid, and sulfuric acid; or with organic acids, such as carbonic acid and methanesulfonic acid.

When 0.5 to 10 moles, and preferably 0.8 to 2 moles, of the amine compound shown in Formula (2) or a salt thereof is used relative to 1 mole of the amine compound shown in Formula (1c) or an active species thereof, the amount of the condensation agent is 0.5 to 20 moles, and preferably 0.8 to 3 moles, relative to 1 mole of the amine compound shown in Formula (1c) or a salt thereof.

Although dependent on the active species or condensation agent used, the reaction is normally carried out in a solvent that is inactive to the reaction at −50 to 150° C., and preferably at −20 to 100° C. Examples of the solvent include halogenated hydrocarbons such as dichloromethane and chloroform; aromatic hydrocarbons such as toluene; ethers such as tetrahydrofuran; esters such as ethyl acetate; alcohols such as methanol and ethanol; water; acetonitrile; N,N-dimethylformamide; N,N-dimethylacetamide; dimethylsulfoxide; and pyridine.

The reaction may proceed smoothly if it is carried out in the presence of about 0.5 to 20 moles, and preferably 0.8 to 5 moles, of a base such as triethylamine, diisopropylethylamine, N-methylmorpholine, N,N-dimethylaniline, 4-(N,N-dimethylamino)pyridine, and pyridine, relative to 1 mole of the amine compound shown in Formula (1c) or an active species thereof.

Note that the compound of the present invention can also be produced by transposing the first step and the second step, and $R^2$ can be converted according to an ordinary, known method if required. The piperazine compound shown in Formula (1a) or a salt thereof, the pyrrolecarboxylic acid compound shown in Formula (1b) or an active species thereof, and the amine compound shown in Formula (1c) or a salt thereof are readily available, or can be produced in accordance with a known method.

Next, the production method of the compound (1c) in the aforementioned Reaction Scheme is shown in Reaction Schemes 2, 3, 4, and 5.

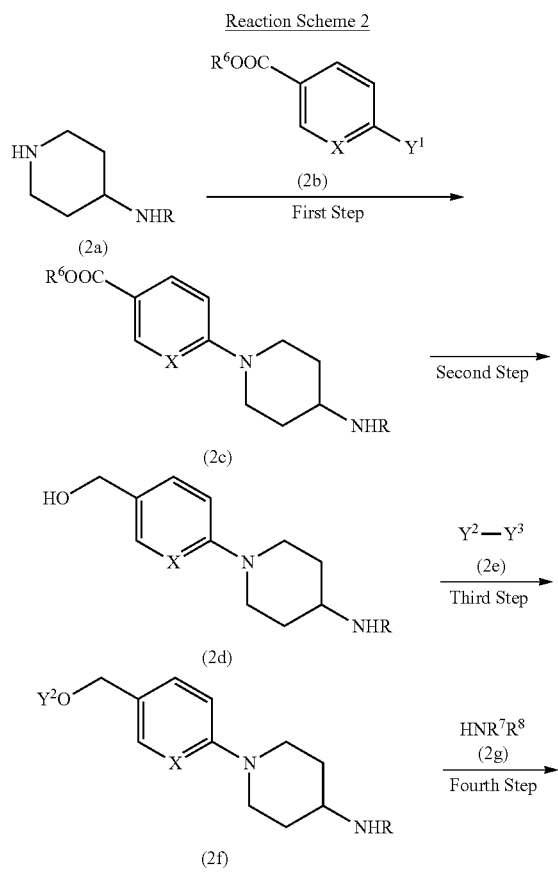

Reaction Scheme 2

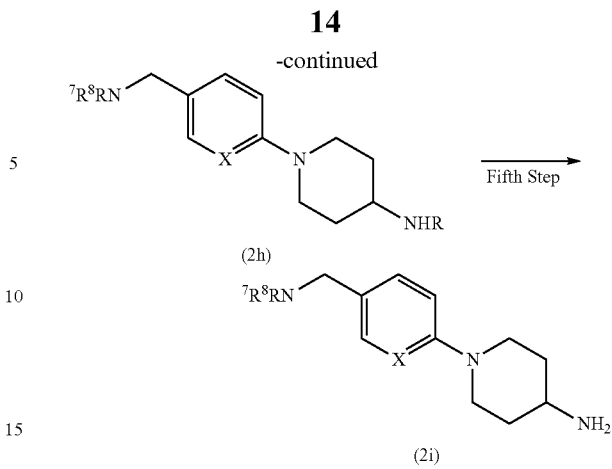

In the above Reaction Scheme 2, X and R are the same as above, $R^6$ is the same as $R^5$ or a silyl protective group such as tert-butyldimethylsilyl, and $R^7$ and $R^8$ are the same as the "substituents" of the "$C_{1-6}$ alkyl groups that may have one or more substituents" represented by $R^2$. $R^7$ and $R^8$ particularly represent substituted or unsubstituted heterocyclic groups; and $Y^1$, $Y^2$ and $Y^3$ represent leaving functional groups.

First Step

Any leaving functional group can be used as $Y^2$ of the compound (2b) in the first step. Examples thereof include halogen such as fluorine and chlorine, methanesulfonyloxy, and p-toluenesulfonyloxy.

In a suitable solvent, using 0.5 to 10 moles, and preferably 0.8 to 2 moles, of the piperidine compound shown in Formula (2a) or a salt thereof relative to 1 mole of the compound shown in Formula (2b), reaction is conducted in the presence of 0.5 to 10 moles, and preferably 0.8 to 3 moles, of a base relative to 1 mole of the compound shown in Formula (2b), at −20 to 180° C., and preferably at 0 to 150° C., for about 1 to 24 hours, thereby obtaining the ester group-containing compound shown in Formula (2c).

Any reaction solvents can be used as long as they do not adversely affect the reaction. Examples thereof include halogenated hydrocarbons such as dichloromethane and chloroform; aromatic hydrocarbons such as toluene; ethers such as tetrahydrofuran; esters such as ethyl acetate; alcohols such as methanol and ethanol; water; acetonitrile; N,N-dimethylformamide; N,N-dimethylacetamide; N-methylpyrrolidone; dimethylsulfoxide; and pyridine. The solvents can be used singly, or in combination.

Examples of usable bases include inorganic bases such as lithium hydroxide, sodium hydroxide, potassium hydroxide, calcium hydroxide, lithium carbonate, sodium carbonate, potassium carbonate, sodium hydride, and potassium hydride, and organic bases such as pyridine, 4-(N,N-dimethylamino)pyridine, triethylamine, diisopropylethylamine, 1,5-diazabicyclo[4.3.0]non-5-ene, 1,8-diazabicyclo[5.4.0]undec-7-en, and potassium tert-butoxide.

In the case where R is hydrogen, in a suitable solvent, using 0.5 to 10 moles, and preferably 0.8 to 2 moles, of an amino group protecting reagent relative to 1 mole of the compound shown in Formula (2c), reaction is conducted in the presence of 0.5 to 10 moles, and preferably 0.8 to 3 moles, of a base relative to 1 mole of the compound shown in Formula (2c), at −20 to 180° C., and preferably at 0 to 150° C., for about 1 to 24 hours, thereby obtaining the compound shown in Formula (2c), which has a protected amino group.

Any reaction solvents can be used as long as they do not adversely affect the reaction. Examples thereof include halogenated hydrocarbons such as dichloromethane and chloroform; aromatic hydrocarbons such as toluene; ethers such as tetrahydrofuran; esters such as ethyl acetate; alcohols such as methanol and ethanol; water; acetonitrile; N,N-dimethylformamide; N,N-dimethylacetamide; N-methylpyrrolidone; dimethylsulfoxide; and pyridine. The solvents can be used singly, or in combination.

Examples of usable amino group protecting reagents include ethyl chlorocarbonate, 9-fluorenylmethylcarbonyl chloride, di-tert-butyl dicarbonate, benzyloxycarbonyl chloride, and benzyl chloride.

Examples of usable bases include inorganic bases such as lithium hydroxide, sodium hydroxide, potassium hydroxide, calcium hydroxide, lithium carbonate, sodium carbonate, potassium carbonate, sodium hydride, and potassium hydride; and organic bases such as pyridine, 4-(N,N-dimethylamino)pyridine, triethylamine, diisopropylethylamine, 1,5-diazabicyclo[4.3.0]non-5-ene, 1,8-diazabicyclo[5.4.0]undec-7-en, and potassium tert-butoxide.

Second Step

In this step, in a suitable solvent, the ester group-containing compound shown in Formula (2c) is reacted in the presence of 0.2 to 10 moles, and preferably 0.5 to 5 moles, of a reducing agent relative to 1 mole of the compound shown in Formula (2c), at −80 to 100° C., and preferably at −50 to 30° C., for about 1 to 24 hours, thereby obtaining the hydroxyl group-containing compound shown in Formula (2d).

Any reaction solvents can be used as long as they do not adversely affect the reaction. Examples thereof include aliphatic hydrocarbons such as n-hexane, aromatic hydrocarbons such as toluene, ethers such as tetrahydrofuran, alcohols such as methanol and ethanol, and water. The solvents can be used singly, or in combination.

Examples of the reducing agent include lithium aluminium hydride, sodium borohydride, borane reagents (for example, diborane), and diisobutylaluminum hydride.

Third Step

In a suitable solvent, using 0.5 to 10 moles, and preferably 0.8 to 2 moles, of the leaving functional group-containing compound shown in Formula (2e) relative to 1 mole of the hydroxyl group-containing compound shown in Formula (2d), reaction is conducted in the presence or absence of 0.5 to 10 moles, and preferably 0.8 to 3 moles, of a base relative to 1 mole of the compound shown in Formula (2d), at −20 to 180° C., and preferably at 0 to 150° C., for about 1 to 24 hours, thereby obtaining the compound shown in Formula (2f).

Any solvents can be used as long as they do not adversely affect the reaction. Examples of suitable solvents include halogenated hydrocarbons such as dichloromethane and chloroform; aromatic hydrocarbons such as toluene; ethers such as tetrahydrofuran; esters such as ethyl acetate; alcohols such as methanol and ethanol; water; acetonitrile; N,N-dimethylformamide; N,N-dimethylacetamide; N-methylpyrrolidone; dimethylsulfoxide; and pyridine. The solvents can be used singly, or in combination.

As the leaving functional group-containing compound shown in Formula (2e), methanesulfonyl chloride, trifluoromethanesulfonyl chloride, p-toluenesulfonyl chloride, benzenesulfonyl chloride, or the like, for example, can be used.

Examples of usable bases include inorganic bases such as sodium hydroxide, calcium hydroxide, sodium carbonate, potassium carbonate, sodium hydride, and potassium hydride; and organic bases such as pyridine, 4-(N,N-dimethylamino)pyridine, triethylamine, diisopropylethylamine, 1,5-diazabicyclo[4.3.0]non-5-ene, 1,8-diazabicyclo[5.4.0]undec-7-en, and potassium tert-butoxide.

Fourth Step

In a suitable solvent, using 0.5 to 10 moles, and preferably 0.8 to 3 moles, of the amine compound shown in Formula (2g) or a salt thereof relative to 1 mole of the compound shown in Formula (2f), reaction is conducted in the presence or absence of 0.5 to 10 moles, and preferably 0.8 to 3 moles, of a base relative to 1 mole of the compound shown in Formula (2f), at −20 to 180° C., and preferably at 0 to 150° C., for 1 to 24 hours, thereby obtaining the compound shown in Formula (2h).

Any solvents can be used, as long as they do not adversely affect the reaction. Examples of suitable solvents include halogenated hydrocarbons such as dichloromethane and chloroform; aromatic hydrocarbons such as toluene; ethers such as tetrahydrofuran; esters such as ethyl acetate; acetonitrile; N,N-dimethylformamide; N,N-dimethylacetamide; N-methylpyrrolidone; dimethylsulfoxide; and pyridine. The solvents can be used singly, or in combination.

Examples of usable bases include inorganic bases such as sodium hydroxide, calcium hydroxide, sodium carbonate, potassium carbonate, and sodium hydride; and organic bases such as pyridine, 4-(N,N-dimethylamino)pyridine, triethylamine, diisopropylethylamine, 1,8-diazabicyclo[5.4.0]undec-7-en, and potassium tert-butoxide. As a base, an excess of the amine compound shown in Formula (2g) may be used.

Fifth Step

In the fifth step, the protective group R of amino group in the compound shown in Formula (2h) is deprotected by an ordinary, known method to obtain the compound shown in Formula (2i).

Deprotection can be carried out under acidic conditions when the protective group R is formyl or tert-butoxycarbonyl; and deprotection can be performed by, for example, a catalytic reduction method when the protective group R is benzyl, benzyloxycarbonyl, or the like.

The compounds (2a), (2b), (2e), and (2g) used in Reaction Scheme 2 are readily available, or can be produced in accordance with a known method.

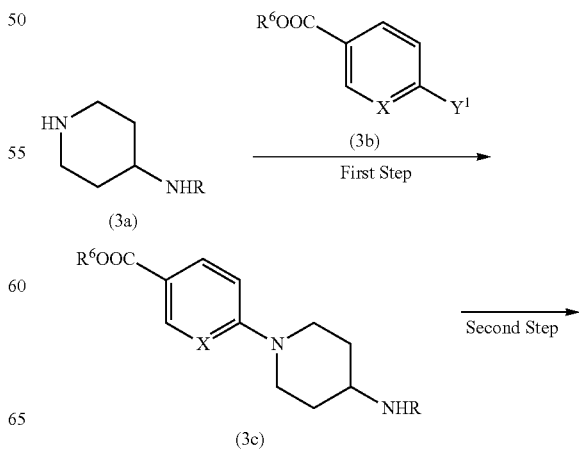

Reaction Scheme 3

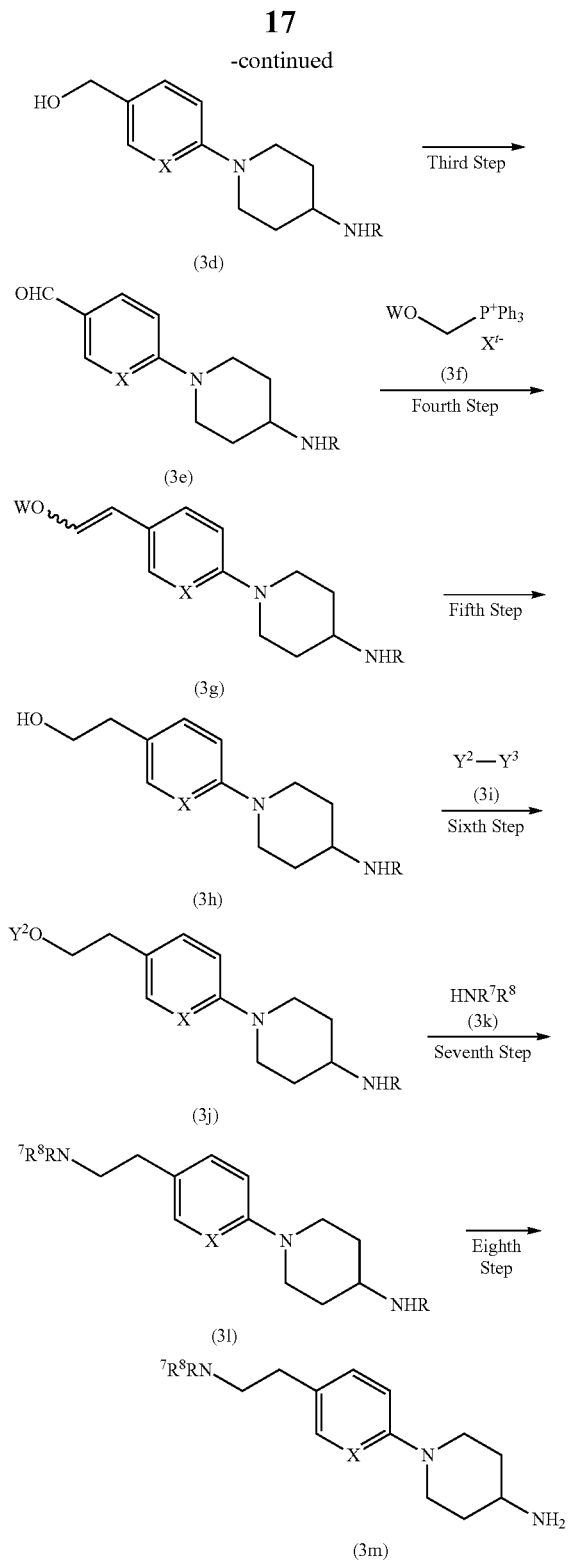

In the above Reaction Scheme 3, W is a protective group of hydroxyl group, and R, $R^6$, $R^7$, $R^8$, X, $Y^1$, $Y^2$ and $Y^3$ are the same as above.

First Step

In this step, the ester group-containing compound represented by Formula (3c) can be obtained in the same manner as in the first step of Reaction Scheme 2.

Second Step

In this step, the hydroxyl group-containing compound represented by Formula (3d) can be obtained in the same manner as in the second step of Reaction Scheme 2.

Third Step

In this step, the hydroxyl group-containing compound represented by Formula (3d) is oxidized by an ordinary, known method to obtain the aldehyde group-containing compound (3e).

In a suitable solvent, reaction is conducted in the presence of 0.8 to 100 moles, and preferably 1 to 30 moles, of an oxidizing agent relative to 1 mole of the compound shown in Formula (3d), at −80 to 180° C., and preferably at −50 to 150° C., for about 1 to 3 days, thereby obtaining the aldehyde group-containing compound shown in Formula (3e).

Any solvents can be used, as long as they do not adversely affect the reaction. Examples of suitable solvents include halogenated hydrocarbons such as dichloromethane, chloroform, and dichloroethane; aromatic hydrocarbons such as toluene; ethers such as tetrahydrofuran; and dimethyl sulfoxide. The solvents can be used singly, or in combination.

Examples of the oxidizing agent include pyridinium chlorochromate (PCC), pyridinium dichromate (PDC), manganese dioxide, sulfur trioxide pyridine complex, Swern oxidation reagent, and Dess-Martin reagent.

Fourth Step

In a suitable solvent, using 0.8 to 10 moles, and preferably 1 to 8 moles, of the Wittig reagent shown in Formula (3f) relative to 1 mole of the aldehyde compound shown in Formula (3e), reaction is conducted in the presence of 0.5 to 10 moles, and preferably 0.8 to 5 moles, of a base relative to 1 mole of the compound shown in Formula (3e), at −20 to 150° C., and preferably at 0 to 80° C., for about 1 to 24 hours, thereby obtaining the compound shown in Formula (3g).

Any solvents can be used, as long as they do not adversely affect the reaction. Examples of suitable solvents include aliphatic hydrocarbons such as n-hexane, aromatic hydrocarbons such as toluene, and ethers such as tetrahydrofuran. The solvents can be used singly, or in combination.

Examples of the protective group W of hydroxyl group in the Wittig reagent shown in Formula (3f) include methyl, methoxymethyl, tetrahydropyranyl, and tert-butyldimethylsilyl.

Examples of usable bases include n-butyllithium, lithium diisopropylamide, lithium hexamethyldisilazide, sodium methoxide, sodium ethoxide, potassium tert-butoxide, and sodium hydride.

Fifth Step

After the protective group of hydroxyl group in the compound shown in Formula (3g) is deprotected in a suitable solvent under acidic conditions, the aldehyde group-containing compound is reacted in a suitable solvent in the presence of 0.2 to 10 moles, and preferably 0.5 to 5 moles, of a reducing agent relative to 1 mole of the compound shown in Formula (3g), at −80 to 100° C., and preferably at −50 to 30° C., for about 1 to 24 hours, thereby obtaining the hydroxyl group-containing compound shown in Formula (3h).

Any reaction solvents can be used, as long as they do not adversely affect the reaction. Examples thereof include aliphatic hydrocarbons such as n-hexane, aromatic hydrocarbons such as toluene, ethers such as tetrahydrofuran, alcohols such as methanol and ethanol, and water. The solvents can be used singly, or in combination.

Examples of the reducing agent include lithium aluminium hydride, sodium borohydride, and sodium cyanoborohydride.

Sixth Step

In this step, the leaving group-containing compound represented by Formula (3j) can be obtained in the same manner as in the third step of Reaction Scheme 2.

Seventh Step

In this step, the amino group-containing compound represented by Formula (3l) can be obtained in the same manner as in the fourth step of Reaction Scheme 2.

Eighth Step

In this step, the amino group-containing compound represented by Formula (3m) can be obtained in the same manner as in the fifth step of Reaction Scheme 2.

The compounds (3a), (3b), (3f), (3i), and (3k) used in Reaction Scheme 3 are readily available, or can be produced in accordance with a known method.

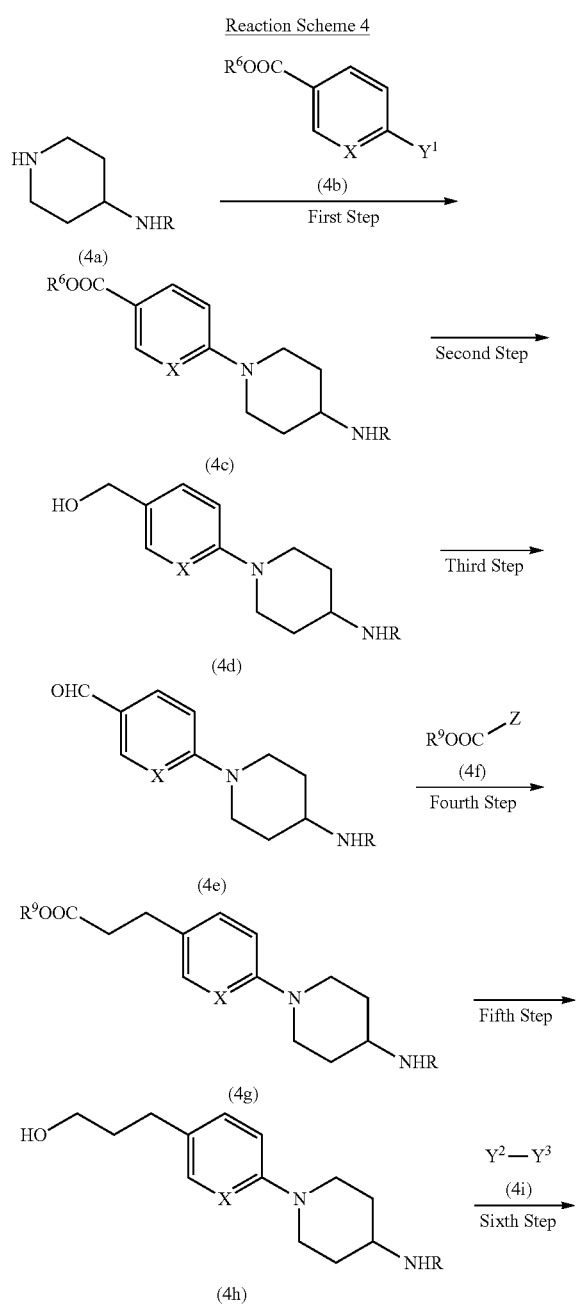

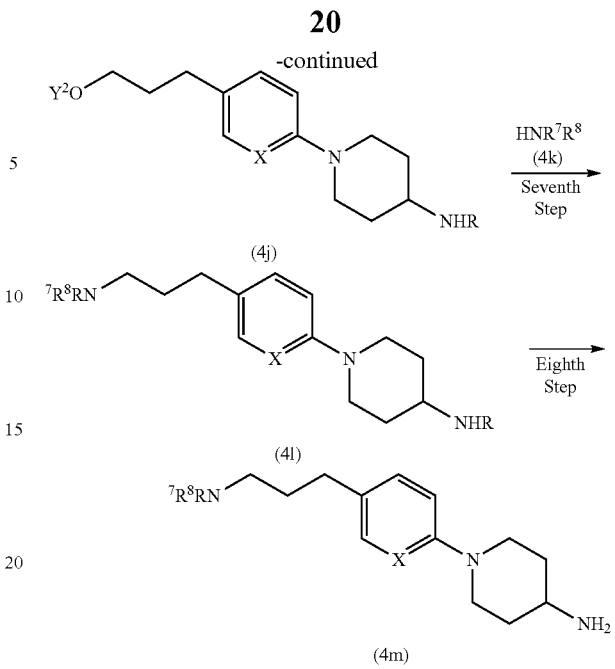

In the above Reaction Scheme 4, $R^9$ is a protective group of ester group, and R, $R^6$, $R^7$, $R^8$, X, $Y^1$, $Y^2$, and $Y^3$ are the same as above. Z is $CH_2P^+R^{10}{}_3Y^{4-}$, $CH=PR^{11}{}_3$, or $CH_2P(O)(OR^{12})_2$. $R^{10}$, $R^{11}$, and $R^{12}$ are lower alkyl such as methyl, ethyl, or butyl, or an aromatic hydrocarbon group such as phenyl; and $Y^4$ is halogen such as chlorine or bromine.

First Step

In this step, the ester group-containing compound represented by Formula (4c) can be obtained in the same manner as in the first step of Reaction Scheme 2.

Second Step

In this step, the hydroxyl group-containing compound represented by Formula (4d) can be obtained in the same manner as in the second step of Reaction Scheme 2.

Third Step

In this step, the aldehyde group-containing compound represented by Formula (4e) can be obtained in the same manner as in the third step of Reaction Scheme 3.

Fourth Step

In a suitable solvent, using 0.8 to 10 moles, and preferably 1 to 8 moles, of the Wittig reagent or Horner-Emmons reagent shown in Formula (4f) relative to 1 mole of the aldehyde compound shown in Formula (4e), reaction is conducted in the presence or absence of 0.5 to 10 moles, and preferably 0.8 to 5 moles, of a base relative to 1 mole of the compound shown in Formula (4e), at −20 to 150° C., and preferably at 0 to 120° C., for about 1 to 24 hours, thereby obtaining an α,β-unsaturated ester group-containing compound.

Any solvents can be used, as long as they do not adversely affect the reaction. Examples of suitable solvents include aliphatic hydrocarbons such as n-hexane, aromatic hydrocarbons such as toluene, and ethers such as tetrahydrofuran. The solvents can be used singly, or in combination.

Examples of the protective group ($R^9$) of ester group in the Wittig reagent or Horner-Emmons reagent shown in (4f) include methyl, ethyl, tert-butyl, tert-butyldimethylsilyl, and benzyl.

Examples of usable bases include inorganic bases such as sodium hydroxide, calcium hydroxide, sodium carbonate, potassium carbonate, sodium hydride, and potassium hydride; and organic bases such as n-butyllithium, lithium diisopropylamide, lithium hexamethyldisilazide, sodium methoxide, sodium ethoxide, potassium tert-butoxide, diisopropylethylamine, and 1,8-diazabicyclo[5.4.0]undec-7-en.

In ethers such as tetrahydrofuran, esters such as ethyl acetate, alcohols such as methanol and ethanol, organic acids such as formic acid and acetic acid, or a mixture of solvents thereof, hydrogen gas is reacted under ordinary pressure or high pressure in the presence of 0.001 to 1 mole, and preferably 0.01 to 0.3 moles, of a reduction catalyst such as carbon-supported palladium, platinum oxide, and Raney nickel, relative to 1 mole of the compound shown in Formula (4e), at 0 to 120° C., and preferably 20 to 100° C., or using 0.5 to 20 moles, and preferably 1 to 10 moles, of formic acid, ammonium formate, cyclohexene, etc., relative to 1 mole of the compound shown in Formula (4e) as a hydrogen source in place of hydrogen gas, reaction is conducted for about 1 to 3 days, thereby obtaining the ester group-containing compound shown in Formula (4g).

Fifth Step

In this step, the hydroxyl group-containing compound represented by Formula (4h) can be obtained in the same manner as in the second step of Reaction Scheme 1.

Sixth Step

In this step, the leaving group-containing compound represented by Formula (4j) can be obtained in the same manner as in the third step of Reaction Scheme 2.

Seventh Step

In this step, the amino group-containing compound represented by Formula (4l) can be obtained in the same manner as in the fourth step of Reaction Scheme 2.

Eighth Step

In this step, the amino group-containing compound represented by Formula (4m) can be obtained in the same manner as in the fifth step of Reaction Scheme 2.

The compounds (4a), (4b), (4f), (4i) and (4k) used in Reaction Scheme 4 are readily available, or can be produced in accordance with a known method.

Reaction Scheme 5

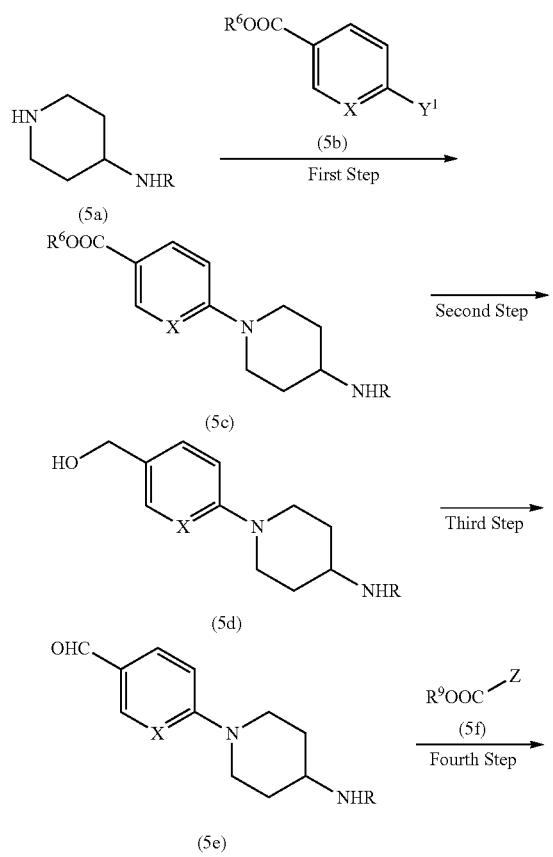

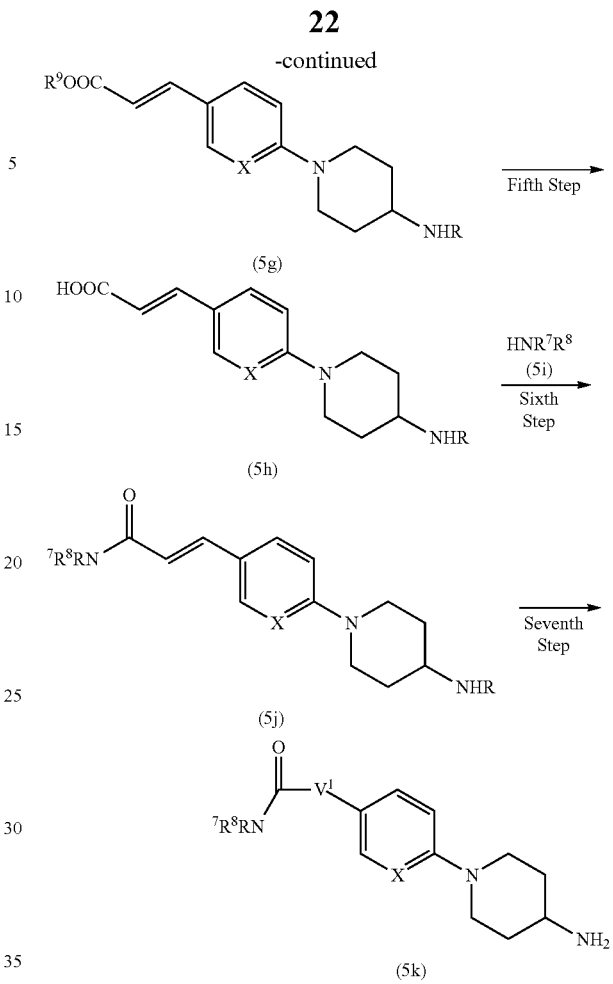

In the above Reaction Scheme 5, $V^1$ is —CH=CH— or —CH$_2$CH$_2$—, and R, $R^6$, $R^7$, $R^8$, $R^9$, X, $Y^1$ and Z are the same as above.

First Step

In this step, the ester group-containing compound represented by Formula (5c) can be obtained in the same manner as in the first step of Reaction Scheme 2.

Second Step

In this step, the hydroxyl group-containing compound represented by Formula (5d) can be obtained in the same manner as in the second step of Reaction Scheme 2.

Third Step

In this step, the aldehyde group-containing compound represented by Formula (5e) can be obtained in the same manner as in the third step of Reaction Scheme 3.

Fourth Step

In a suitable solvent, using 0.8 to 10 moles, and preferably 1 to 8 moles, of the Wittig reagent or Horner-Emmons reagent shown in Formula (5f) relative to 1 mole of the aldehyde compound shown in Formula (5e), reaction is conducted in the presence or absence of 0.5 to 10 moles, and preferably 0.8 to 5 moles, of a base relative to 1 mole of the compound shown in Formula (5e), at −20 to 150° C., and preferably at 0 to 120° C., for about 1 to 24 hours, thereby obtaining the α,β-unsaturated ester group-containing compound shown in Formula (5g).

Any solvents can be used, as long as they do not adversely affect the reaction. Examples of suitable solvents include aliphatic hydrocarbons such as n-hexane, aromatic hydrocarbons such as toluene, and ethers such as tetrahydrofuran. The solvents can be used singly, or in combination.

Examples of the protective group ($R^9$) of ester group in the Wittig reagent or Horner-Emmons reagent shown in (5f) include methyl, ethyl, tert-butyl, tert-butyldimethylsilyl, and benzyl.

Examples of usable bases include inorganic bases such as sodium hydroxide, calcium hydroxide, sodium carbonate, potassium carbonate, sodium hydride, and potassium hydride; and organic bases such as n-butyllithium, lithium diisopropylamide, lithium hexamethyldisilazide, sodium methoxide, sodium ethoxide, potassium tert-butoxide, diisopropylethylamine, and 1,8-diazabicyclo[5.4.0]undec-7-en.

Fifth Step

In this step, the ester group of the ester group-containing compound shown in Formula (5g) is deprotected by an ordinary, known method to obtain the carboxylic acid compound shown in Formula (5h).

Sixth Step

In this step, condensation reaction with the amine compound shown in Formula (5i) or a salt thereof is conducted in the same manner as in the first step of Reaction Scheme 1 to obtain the amide compound shown in Formula (5j).

Seventh Step

In this step, when $V^1$ in the compound shown in Formula (5k) is —CH=CH—, the amino group-containing compound shown in Formula (5k) can be obtained in the same manner as in the fifth step of Reaction Scheme 2.

In this step, when $V^1$ in the compound shown in Formula (5k) is —CH$_2$CH$_2$—, in ethers such as tetrahydrofuran, esters such as ethyl acetate, alcohols such as methanol and ethanol, organic acid such as formic acid and acetic acid, or a mixture of solvents thereof, hydrogen gas is reacted under ordinary pressure or high pressure in the presence of 0.001 to 1 mole, and preferably 0.01 to 0.3 moles, of a reduction catalyst such as carbon-supported palladium, platinum oxide, and Raney nickel, relative to 1 mole of the compound shown in Formula (5j), at 0 to 120° C., and preferably 20 to 100° C., or using 0.5 to 20 moles, and preferably 1 to 10 moles, of formic acid, ammonium formate, cyclohexene, etc. relative to 1 mole of the compound shown in Formula (5j) as a hydrogen source in place of hydrogen gas, reaction is conducted for about 1 to 3 days, and then, the amino group-containing compound shown in Formula (5k) can be obtained in the same manner as in the fifth step of Reaction Scheme 2.

The compounds (5a), (5b), (5f), and (5i) used in Reaction Scheme 5 are readily available, or can be produced in accordance with a known method.

The compounds (3e), (4e), and (5e) used in Reaction Schemes 3 to 5 can also be produced as shown in Reaction Scheme 6 described below.

Reaction Scheme 6

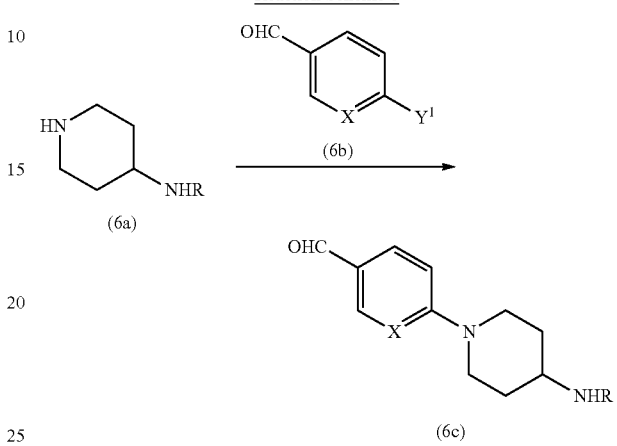

In the above Reaction Scheme 6, R is a protective group of amino group, and X and $Y^1$ are the same as above.

In this step, the aldehyde group-containing compound shown in Formula (6c) can be obtained in the same manner as in the first step of Reaction Scheme 2 by using the aldehyde group-containing compound shown in Formula (6b) instead of the ester group-containing compound shown in Formula (2b).

Of the compounds of the present invention, compounds having particular functional groups may be converted to other compounds of the invention by chemically modifying these groups, as shown in the following Reaction Scheme 7.

Reaction Scheme 7

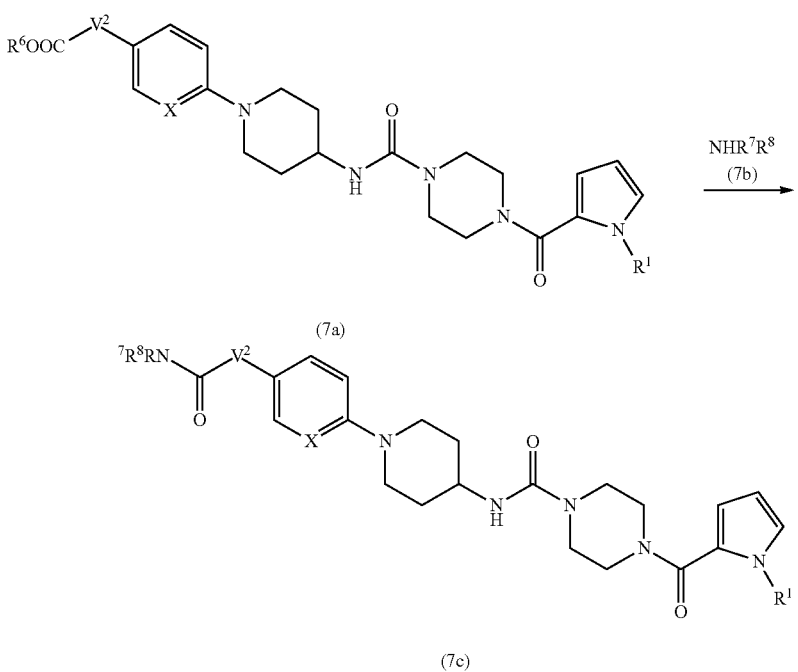

In the above Reaction Scheme 7, $V^2$ is a $C_{0-3}$ alkylene group or —CH=CH—, and $R^1$, $R^6$, $R^7$, $R^8$ and X are the same as above. A $C_0$ alkylene group means a single bond.

In this step, the carboxylic acid compound obtained by deprotecting the ester group of the ester group-containing compound shown in Formula (7a) by an ordinary, known method, or an active species thereof is condensed in the same manner as in the first step of Reaction Scheme 1 with the amine compound represented by Formula (7b), or a salt thereof, to obtain the amide compound shown in Formula (7c).

If one or more asymmetric carbons are present in the compound (I), which is useful as an active ingredient of the medicine of the present invention, optical isomers due to asymmetric carbon atoms (enantiomers and diastereomers) and other isomers may be present. The present invention encompasses isomers that have been isolated, and mixtures thereof.

The compound (I), which is useful as an active ingredient of the medicine of the present invention, encompasses pharmaceutically acceptable prodrugs. Pharmaceutically acceptable prodrugs are compounds having functional groups that can be converted, under chemical conditions, such as solvolysis, or under physiological conditions, into amino, hydroxyl, carboxyl, carbonyl, or like functional groups of the compound (I), which is an active ingredient of the medicine of the present invention. Representative functional groups of prodrugs include the groups mentioned in "*Iyakuhin no Kaihatsu* [Development of Pharmaceuticals]," Vol. 7, pp. 163-198, Hirokawa Publishing (1990).

The compound (I), which is useful as an active ingredient of the medicine of the present invention, may form an acid addition salt or a salt with a base. Such salts are included in the present invention insofar as they are pharmaceutically acceptable. Specific examples thereof include acid addition salts with inorganic acids, such as hydrochloric acid, hydrobromic acid, hydroiodic acid, sulfuric acid, nitric acid, phosphoric acid, etc., or organic acids, such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, para-toluenesulfonic acid, glutamic acid, etc.; salts with inorganic bases, such as sodium, potassium, magnesium, calcium, aluminium, etc., organic bases such as methylamine, ethylamine, meglumine, ethanolamine, etc., or basic amino acids such as lysine, arginine, ornithine, etc.; and ammonium salts.

The present invention further encompasses the hydrates, solvates, and crystal polymorphs of the compound (I), which is useful as an active ingredient of the medicine of the present invention, and pharmaceutically acceptable salts thereof.

When a pharmaceutical composition contains the piperazine compound or a salt thereof according to the present invention, a pharmaceutical carrier can be added, if required, thereby forming a suitable dosage form according to prevention and treatment purposes. Examples of the dosage form include oral preparations, injections, suppositories, ointments, patches, etc. Of these, oral preparations are preferable. Such dosage forms can be formed by common preparation methods known to persons skilled in the art.

As the pharmaceutical carrier, various organic or inorganic carrier materials commonly used as preparation materials may be blended as an excipient, binder, disintegrant, lubricant, or colorant in solid preparations; or as a solvent, solubilizing agent, suspending agent, isotonizing agent, buffer, or soothing agent in liquid preparations. Moreover, a pharmaceutical preparation additive, such as an antiseptic, anti-oxidant, colorant, sweetener, and stabilizer may also be used, if required.

Oral solid preparations are prepared as follows. An excipient, optionally together with a binder, disintegrant, lubricant, colorant, sweetening/flavoring agent, etc., is added into the compound of the present invention to produce tablets, coated tablets, granules, powders, capsules, or the like, using an ordinary method.

Examples of excipients include lactose, sucrose, D-mannitol, glucose, starch, calcium carbonate, kaolin, microcrystalline cellulose, and silicic acid anhydride.

Examples of binders include water, ethanol, 1-propanol, 2-propanol, simple syrup, liquid glucose, liquid α-starch, liquid gelatin, D-mannitol, carboxymethyl cellulose, hydroxypropyl cellulose, hydroxypropyl starch, methyl cellulose, ethyl cellulose, shellac, calcium phosphate, and polyvinylpyrrolidone.

Examples of disintegrants include dry starch, sodium alginate, agar powder, sodium hydrogen carbonate, calcium carbonate, sodium lauryl sulfate, stearic acid monoglyceride, and lactose.

Examples of lubricants include purified talc, sodium stearate, magnesium stearate, borax, and polyethylene glycol.

Examples of colorants include titanium oxide and iron oxide.

Examples of sweetening/flavoring agents include sucrose, wild orange peel, citric acid, and tartaric acid.

Oral liquid preparations are produced as follows. A sweetening agent, buffer, stabilizer, flavoring agent, etc., is added into the compound of the present invention to produce an internal liquid medicine, a syrup, an elixir, or the like using an ordinary method. In this case, sweetening/flavoring agents as described above are usable. Examples of buffers include sodium citrate, and examples of stabilizers include tragacanth, gum arabic, and gelatin. If necessary, an enteric coating or a coating to increase the persistence of effects can be provided by methods known for oral preparations. Examples of coating agents include hydroxypropylmethyl cellulose, ethyl cellulose, hydroxymethyl cellulose, hydroxypropyl cellulose, polyoxy ethylene glycol, and Tween 80 (a registered trademark).

Injections are prepared as follows. A pH adjuster, buffer, stabilizer, isotonizing agent, topical anesthetic, etc., is added into the compound of the present invention to produce a subcutaneous injection, an intramuscular injection, or an intravenous injection using an ordinary method. Examples of usable pH adjusters and buffers in this case include sodium citrate, sodium acetate, and sodium phosphate. Examples of usable stabilizers include sodium pyrosulfite, EDTA, thioglycolic acid, and thiolactic acid. Examples of usable topical anesthetics include procaine hydrochloride and lidocaine hydrochloride. Examples of usable isotonizing agents include sodium chloride, glucose, D-mannitol, and glycerin.

Suppositories are prepared as follows. A pharmaceutical carrier known in the art, such as polyethylene glycol, lanolin, cacao butter, and fatty acid triglyceride, is added into the compound of the present invention, optionally together with Tween 80 (a registered trademark) or a like surfactant, followed by production using an ordinary method.

Ointments are prepared as follows. An ordinary base, stabilizer, wetting agent, preservative, etc., is added as required into the compound of the present invention, and mixed and formulated using an ordinary method. Examples of bases include liquid paraffin, white petrolatum, white beeswax, octyldodecyl alcohol, and paraffin. Examples of preservatives include methyl parahydroxybenzoate, ethyl parahydroxybenzoate, and propyl parahydroxybenzoate.

Patches can be prepared by coating a general support with the above ointment, cream, gel, paste, etc., using an ordinary method. Examples of supports include woven or nonwoven fabrics made from cotton, staple fibers, and chemical fibers; and films and foam sheets of soft vinyl chloride, polyethylene, and polyurethane.

The amount of the compound of the present invention to be contained in such a dosage unit form varies depending on the condition of the patient or on the dosage form. The desirable amount in one dosage unit form is about 0.05 to about 1,000 mg in the case of an oral preparation, about 0.01 to about 500 mg in the case of an injection, and about 1 to about 1,000 mg in the case of a suppository.

The daily dose of the medicine in such a dosage form depends on the condition, body weight, age, gender, etc., of the patient. For example, the daily dose for an adult (body weight: 50 kg) may be generally about 0.05 to about 5,000 mg, and preferably 0.1 to 1,000 mg, and is preferably administered in one or in two to three divided doses per day.

Since the H-PGDS inhibiting action is attained in mammals, and especially humans, by administrating a medicine containing the compound of the present invention, the compound of the present invention is useful in treating, preventing, or improving diseases caused by PGD2 generated by the synthase or metabolite thereof. Examples of diseases to be treated, prevented, or improved by a medicine containing the compound of the present invention include allergic disease such as bronchial asthma, pollinosis, allergic rhinitis, sinusitis, otitis media, allergic conjunctivitis, spring catarrh, atopic dermatitis, contact dermatitis, and food allergies.

In addition, the medicine containing the compound of the present invention is useful in treating, preventing, or improving inflammatory diseases including chronic obstructive pulmonary disease, interstitial pneumonia, hypersensitivity pneumonitis, eosinophilic pneumonia, articular rheumatism, degenerative arthritis, multiple sclerosis, amyotrophic lateral sclerosis, inflammatory bowel disease, skin diseases (psoriasis, eczema, erythema, itch syndrome, pimples, etc.), myositis, muscular dystrophy, post-PTCA restenosis, chronic obstructive arterial disease, reperfusion injury, and graft rejection reaction; mucus secretion problems; reproductive problems; blood coagulation disorders; sleep disorders; pain; vision problems; obesity; immunopathy; and autoimmune diseases.

The medicine containing the compound of the present invention is expected to prevent exacerbation of Alzheimer disease or brain damage, and/or improve the prognosis after brain damage. In addition, since it can inhibit cell neoplastic transformation and metastatic tumor growth, it is also useful in cancer therapy.

Moreover, it is useful in the treatment and/or prevention of proliferative disorders due to PGD2 or its metabolites, such as fibroblast proliferation, diabetic retinopathy, and tumor angiogenesis. Furthermore, since it can suppress PGD2-induced smooth muscle contraction, it can also be used in the treatment and/or prevention of infertility, dysmenorrhea, premature delivery, and eosinophile-leucocyte-related disorders.

EXAMPLES

The present invention is described in detail below with reference to Reference Examples, Examples, and Test Examples, which are not intended to limit the scope of the invention.

In the following description, $^1$H-NMR spectra were measured using TMS (tetramethylsilane) as an internal standard, and the chemical shifts are indicated by δ (ppm). With respect to the chemical shifts, absorption patterns, coupling constants (J), and numbers of protons are indicated in parentheses.

The following symbols are used for absorption patterns: s=singlet, d=doublet, t=triplet, q=quartet, dd=double doublet, m=multiplet, br=broad, and brs=broad singlet.

Moreover, the following symbols are used for structural formulas of compounds: Me=methyl and Et=ethyl.

Example 1(1)

4-(4-aminopiperidin-1-yl)-benzoic acid tert-butyl ester 4-fluorobenzoic acid tert-butyl ester (19.6 g, 100 mmol) was dissolved in dimethyl sulfoxide (hereinafter referred to as DMSO) (50 ml), and potassium carbonate (20.7 g, 150 mmol) and 4-aminopiperidine (11.0 g, 110 mmol) were added thereto, followed by stirring at 120° C. for 17 hours. After the reaction mixture was cooled to room temperature, water was added to the mixture, and the precipitate was collected by filtration, thereby obtaining 4-(4-aminopiperidin-1-yl)-benzoic acid tert-butyl ester (23.3 g, 84%) as a milky-white solid.

$^1$H-NMR (CDCl$_3$): δ (ppm) 1.15-1.75 (m, 4H), 1.57 (s, 9H), 1.83-2.04 (m, 2H), 2.81-3.02 (m, 3H), 3.72-3.94 (m, 2H), 6.85 (d, J=9.2 Hz, 2H), 7.85 (d, J=9.2 Hz, 2H)

Example 1(2)

4-(4-(4-((1-methylpyrrol-2-yl)-carbonyl)-1-piperazinecarbamoyl)piperidin-1-yl)-benzoic acid tert-butyl ester 4-nitrophenyl chloroformate (2.42 g, 12 mmol) was dissolved in tetrahydrofuran (hereinafter referred to as THF) (50 ml), and a THF (30 ml) solution of the 4-(4-aminopiperidin-1-yl)-benzoic acid tert-butyl ester (2.76 g, 10 mmol) obtained in Example 1(1) was added dropwise at −30° C. After stirring for 30 minutes at the same temperature, 1-[(1-methyl-1H-pyrrol-2-yl)carbonyl]piperazine hydrochloride (2.53 g, 11 mmol) and triethylamine (5.6 ml, 40 mmol) were added to the mixture, followed by stirring at room temperature for 15 hours. A saturated sodium bicarbonate aqueous solution was added to the reaction mixture, followed by extraction with ethyl acetate. The organic layer was washed with water and saturated sodium chloride, and then dried over anhydrous sodium sulfate. After the desiccant was filtered off, the residue obtained by evaporation under reduced pressure was purified using medium-pressure silica gel flash column chromatography (methanol:chloroform=0:1 to 1:30), thereby obtaining 4-(4-(4-((1-methylpyrrol-2-yl)-carbonyl)-1-piperazinecarbamoyl)piperidin-1-yl)-benzoic acid tert-butyl ester (3.73 g, 75%) as a milky-white solid.

$^1$H-NMR (CDCl$_3$): δ (ppm) 1.40-1.68 (m, 2H), 1.57 (s, 9H), 1.98-2.17 (m, 2H), 2.91-3.08 (m, 2H), 3.35-3.53 (m 4H), 3.79 (s, 3H), 3.68-4.00 (m, 7H), 4.33 (d, J=7.1 Hz, 1H), 6.06-6.18 (m, 1H), 6.30-6.41 (m, 1H), 6.68-6.78 (m, 1H), 6.85 (d, J=9.1 Hz, 2H), 7.86 (d, J=9.1 Hz, 2H)

Example 1

4-(4-(4-((1-methylpyrrol-2-yl)-carbonyl)-1-piperazinecarbamoyl)piperidin-1-yl)-benzoic acid (compound 1)

The 4-(4-(4-((1-methylpyrrol-2-yl)-carbonyl)-1-piperazinecarbamoyl)piperidin-1-yl)-benzoic acid tert-butyl ester (2.48 g, 5.0 mmol) obtained in Example 1(2) was dissolved in formic acid (10 ml), followed by stirring for 5 hours at 60° C. Water was added to the residue obtained by concentration under reduced pressure, and the precipitate was collected by filtration, thereby obtaining 4-(4-(4-((1-methylpyrrol-2-yl)-carbonyl)-1-piperazinecarbamoyl)piperidin-1-yl)-benzoic acid (2.12 g, 97%) as a milky-white solid.

$^1$H-NMR (DMSO-$d_6$): δ (ppm) 1.32-1.60 (m, 2H), 1.75-1.95 (m, 2H), 2.82-3.10 (m, 2H), 3.66 (s, 3H), 3.15-4.06 (m, 11H), 6.00-6.12 (m, 1H), 6.30-6.48 (m, 2H), 6.85-6.97 (m, 1H), 6.95 (d, J=9.0 Hz, 2H), 7.76 (d, J=9.0 Hz, 2H), 12.21 (br, 1H)

Example 2

4-((1-methylpyrrol-2-yl)-carbonyl)-N-(1-(4-(pyridin-3-ylmethylcarbamoyl)phenyl)-piperidin-4-yl)-1-piperazinecarboxamide (compound 2)

The 4-(4-(4-((1-methylpyrrol-2-yl)-carbonyl)-1-piperazinecarbamoyl)piperidin-1-yl)-benzoic acid (440 mg, 1.0 mmol) obtained in Example 1 was dissolved in N,N-dimethylformamide (hereinafter referred to as DMF) (3.0 ml), and 1-ethyl-3-(3-dimethylamino propyl)carbodiimide hydrochloride (hereinafter referred to as WSCD) (230 mg, 1.2 mmol), 1-hydroxybenzotriazole monohydrate (hereinafter referred to as HOBt) (168 mg, 1.1 mmol), and 3-aminomethylpyridine (0.12 ml, 1.2 mmol) were added thereto, followed by stirring under heat at 60° C. for 3 hours. After cooling to room temperature, a saturated sodium bicarbonate aqueous solution was added to the mixture, and the precipitate was collected by filtration and dried under heat under reduced pressure, thereby obtaining 4-((1-methylpyrrol-2-yl)-carbonyl)-N-(1-(4-(pyridin-3-ylmethylcarbamoyl)phenyl)-piperidin-4-yl)-1-piperazinecarboxamide (223 mg, 42%) as a milky-white solid.

$^1$H-NMR (CDCl$_3$): δ (ppm) 1.36-1.60 (m, 2H), 1.98-2.18 (m, 2H), 2.85-3.08 (m, 2H), 3.30-3.48 (m 4H), 3.78 (s, 3H), 3.65-4.00 (m, 7H), 4.37-4.50 (m, 1H), 4.64 (d, J=5.8 Hz, 2H), 6.06-6.14 (m, 1H), 6.31-6.39 (m, 1H), 6.41-6.56 (m, 1H), 6.67-6.76 (m, 1H), 6.88 (d, J=9.1 Hz, 2H), 7.20-7.35 (m, 1H), 7.59-7.78 (m, 3H), 8.47-8.65 (m, 2H)

Example 3

4-((1-methylpyrrol-2-yl)-carbonyl)-N-(1-(4-(2-morpholinoethylcarbamoyl)-phenyl)-piperidin-4-yl)-1-piperazinecarboxamide (compound 3)

Following the procedure of Example 2, aminoethylmorpholine was used instead of 3-aminomethylpyridine, thereby obtaining 4-((1-methylpyrrol-2-yl)-carbonyl)-N-(1-(4-(2-morpholinoethylcarbamoyl)-phenyl)-piperidin-4-yl)-1-piperazinecarboxamide (62%) as a milky-white solid.

$^1$H-NMR (CDCl$_3$): δ (ppm) 1.41-1.63 (m, 2H), 1.99-2.17 (m, 2H), 2.38-2.69 (m, 6H), 2.87-3.09 (m, 2H), 3.33-3.60 (m, 6H), 3.79 (s, 3H), 3.62-4.00 (m, 11H), 4.45 (d, J=7.3 Hz, 1H), 6.05-6.14 (m, 1H), 6.29-6.40 (m, 1H), 6.55-6.78 (m, 2H), 6.90 (d, J=8.9 Hz, 2H), 7.68 (d, J=8.9 Hz, 2H)

Example 4

4-((1-methylpyrrol-2-yl)-carbonyl)-N-(1-(4-(4-morpholinylcarbonyl)phenyl)-piperidin-4-yl)-1-piperazinecarboxamide (compound 4)

Following the procedure of Example 2, morpholine was used instead of 3-aminomethylpyridine, thereby obtaining 4-((1-methylpyrrol-2-yl)-carbonyl)-N-(1-(4-(4-morpholinylcarbonyl)phenyl)-piperidin-4-yl)-1-piperazinecarboxamide (52%) as a milky-white solid.

$^1$H-NMR (CDCl$_3$): δ (ppm) 1.40-1.67 (m, 2H), 2.01-2.24 (m, 2H), 2.87-3.03 (m, 2H), 3.34-3.57 (m 4H), 3.79 (s, 3H), 3.59-4.00 (m, 15H), 4.32-4.45 (m, 1H), 6.05-6.14 (m, 1H), 6.30-6.39 (m, 1H), 6.68-6.77 (m, 1H), 6.89 (d, J=8.9 Hz, 2H), 7.34 (d, J=8.9 Hz, 2H)

Example 5

4-((1-methylpyrrol-2-yl)-carbonyl)-N-(1-(4-(1-piperidinylcarbonyl)phenyl)-piperidin-4-yl)-1-piperazinecarboxamide (compound 5)

Following the procedure of Example 2, piperidine was used instead of 3-aminomethylpyridine, thereby obtaining 4-((1-methylpyrrol-2-yl)-carbonyl)-N-(1-(4-(1-piperidinylcarbonyl)phenyl)-piperidin-4-yl)-1-piperazinecarboxamide (68%) as a milky-white solid.

$^1$H-NMR (CDCl$_3$): δ (ppm) 1.40-1.74 (m, 8H), 2.00-2.19 (m, 2H), 2.79-3.03 (m, 2H), 3.38-4.05 (m, 15H), 3.79 (s, 3H), 4.33-4.44 (m, 1H), 6.02-6.11 (m, 1H), 6.31-6.38 (m, 1H), 6.72 (brs, 1H), 6.89 (d, J=8.9 Hz, 2H), 7.32 (d, J=8.9 Hz, 2H)

Example 6

4-((1-methylpyrrol-2-yl)-carbonyl)-N-(1-(4-(1-pyrrolidinylcarbonyl)phenyl)-piperidin-4-yl)-1-piperazinecarboxamide (compound 6)

Following the procedure of Example 2, pyrrolidine was used instead of 3-aminomethylpyridine, thereby obtaining 4-((1-methylpyrrol-2-yl)-carbonyl)-N-(1-(4-(1-pyrrolidinylcarbonyl)phenyl)-piperidin-4-yl)-1-piperazinecarboxamide (72%) as a milky-white solid.

$^1$H-NMR (CDCl$_3$): δ (ppm) 1.38-1.72 (m, 2H), 1.82-2.21 (m, 6H), 2.82-3.05 (m, 2H), 3.40-4.02 (m, 15H), 3.78 (s, 3H), 4.34-4.48 (m, 1H), 6.05-6.12 (m, 1H), 6.31-6.36 (m, 1H), 6.68-6.64 (m, 1H), 6.88 (d, J=8.9 Hz, 2H), 7.48 (d, J=8.9 Hz, 2H)

Example 7(1)

4-(4-aminopiperidin-1-yl)-benzoic acid ethyl ester

Following the procedure of Example 1(1), 4-fluorobenzoic acid ethyl ester was used instead of 4-fluorobenzoic acid tert-butyl ester, thereby obtaining 4-(4-aminopiperidin-1-yl)-benzoic acid ethyl ester (98%) as a yellow solid.

$^1$H-NMR (CDCl$_3$): δ (ppm) 1.33-1.40 (m, 2H), 1.36 (t, J=7.0 Hz, 3H), 1.93 (d, J=5.4 Hz, 2H), 2.85-2.96 (m, 4H), 3.83 (d, J=13.2 Hz, 2H), 4.32 (q, J=7.0 Hz, 2H), 4.74 (br, 1H), 6.90 (d, J=9.2 Hz, 2H), 7.91 (d, J=9.2 Hz, 2H).

Example 7(2)

4-(4-benzyloxycarbonylaminopiperidin-1-yl)-benzoic acid ethyl ester

The 4-(4-aminopiperidin-1-yl)-benzoic acid ethyl ester (15.7 g, 63.2 mmol) obtained in Example 7(1) was dissolved in THF (200 ml), and a 2M sodium carbonate aqueous solution (63 ml) was added thereto. Subsequently, benzyloxycarbonyl chloride (11.7 ml, 82.2 mmol) was added thereto, followed by stirring at room temperature for 2 hours. Water was added to the reaction mixture, followed by extraction with ethyl acetate. The organic layer was washed with water and saturated sodium chloride, and then dried over anhydrous sodium sulfate. After the desiccant was filtered off, the solid obtained by evaporation under reduced pressure was collected by filtration and dried under reduced pressure, thereby obtaining 4-(4-benzyloxycarbonylaminopiperidin-1-yl)-benzoic acid ethyl ester (18.0 g, 74%) as a white solid.

$^1$H-NMR (CDCl$_3$): δ (ppm) 1.36 (t, J=7.0 Hz, 3H), 1.38-1.62 (m, 2H), 2.04-2.10 (m, 2H), 2.98 (t, J=11.1 Hz, 2H), 3.75-3.85 (m, 3H), 4.32 (q, J=7.0 Hz, 2H), 4.71 (br, 1H), 5.11 (s, 2H), 6.85 (d, J=9.2 Hz, 2H), 7.26-7.36 (m, 5H), 7.91 (d, J=9.2 Hz, 2H).

Example 7(3)

4-(4-benzyloxycarbonylaminopiperidin-1-yl)-benzaldehyde

The 4-(4-benzyloxycarbonylaminopiperidin-1-yl)-benzoic acid ethyl ester (13.6 g, 35.6 mmol) obtained in Example 7 (2) was dissolved in dichloromethane (150 ml), and a diisobutylaluminum hydride-hexane solution (91 ml, 89.0 mmol) was added thereto, followed by stirring at −78° C. for 1 hour. Methanol was added to the reaction mixture, and then saturated sodium chloride was added thereto, followed by stirring. After the insoluble material was filtered with Celite, the solvent was evaporated from the filtrate under reduced pressure. The obtained residue was dissolved in dichloroethane (180 ml), and manganese dioxide (38.0 g) was added thereto, followed by stirring at 60° C. for 21 hours. After the insoluble material was filtered with Celite, the solvent was evaporated from the filtrate under reduced pressure, thereby obtaining 4-(4-benzyloxycarbonylaminopiperidin-1-yl)-benzaldehyde (7.0 g, 58%) as a white solid.

$^1$H-NMR (CDCl$_3$): δ (ppm) 1.43-1.56 (m, 2H), 2.08 (d, J=9.7 Hz, 2H), 3.10 (t, J=11.1 Hz, 2H), 3.80-3.90 (m, 3H), 4.70 (br, 1H), 5.11 (s, 2H), 6.91 (d, J=8.9 Hz, 2H), 7.26-7.36 (m, 5H), 7.74 (d, J=8.9 Hz, 2H), 9.77 (s, 1H).

Example 7(4)

N-(4-(2-hydroxyethyl)phenyl)-4-benzyloxycarbonylaminopiperidine

Methoxymethyltriphenylphosphonium chloride (16.2 g, 47.3 mmol) was dissolved in THF (300 ml), and an n-butyllithium-hexane solution (29.0 ml, 45.4 mmol) was added dropwise at 0° C., followed by stirring for 30 minutes. Subsequently, the 4-(4-benzyloxycarbonylaminopiperidin-1-yl)-benzaldehyde (3.2 g, 9.46 mmol) obtained in Example 7(3) was added thereto, followed by stirring at room temperature for 17 hours. A saturated sodium bicarbonate aqueous solution was added to the reaction mixture, followed by extraction with chloroform. The solvent was evaporated from the organic layer under reduced pressure, and the obtained residue was purified using medium-pressure silica gel flash column chromatography (NH silica gel, ethyl acetate:hexane=1:4), thereby obtaining a crude enol ether as a mixture. The obtained mixture was dissolved in ethyl acetate (30 ml), and a 6N hydrochloric acid aqueous solution (6.0 ml) was added thereto, followed by stirring for one hour. The reaction mixture was neutralized with the addition of a saturated sodium bicarbonate aqueous solution, followed by extraction with chloroform. The solvent was evaporated from the organic layer under reduced pressure. The obtained residue was dissolved in THF (15 ml) and methanol (15 ml), and sodium borohydride (155 mg, 4.09 mmol) was added thereto, followed by stirring at 0° C. for 1 hour. After a saturated ammonium chloride aqueous solution was added to the reaction mixture, water was added to the residue obtained by concentration under reduced pressure. The precipitate was collected by filtration, thereby obtaining N-(4-(2-hydroxyethyl)phenyl)-4-benzyloxycarbonylaminopiperidine (960 mg, 29%) as a white solid.

$^1$H-NMR (CDCl$_3$): δ (ppm) 1.43-1.59 (m, 2H), 2.06 (d, J=10.3 Hz, 2H), 2.76-2.85 (m, 4H), 3.53-3.80 (m, 5H), 4.70-4.80 (m, 2H), 5.11 (s, 2H), 6.88 (d, J=8.6 Hz, 2H), 7.11 (d, J=8.6 Hz, 2H), 7.26-7.36 (m, 5H).

Example 7(5)

N-(4-(2-tosyloxyethyl)phenyl)-4-benzyloxycarbonylaminopiperidine

The N-(4-(2-hydroxyethyl)phenyl)-4-benzyloxycarbonylaminopiperidine (1.38 g, 3.89 mmol) obtained in Example 7 (4) was dissolved in pyridine (7.5 ml), and p-toluenesulfonyl chloride (960 mg, 5.04 mmol) was added thereto under ice-cooling, followed by stirring for 4 hours. Water was added to the reaction mixture, and the precipitate was collected by filtration, thereby obtaining N-(4-(2-tosyloxyethyl)phenyl)-4-benzyloxycarbonylaminopiperidine (1.35 g, 68%) as a yellow solid.

$^1$H-NMR (CDCl$_3$): δ (ppm) 1.48-1.62 (m, 2H), 2.06 (d, J=9.2 Hz, 2H), 2.43 (s, 3H), 2.78-2.89 (m, 4H), 3.52-3.65 (m, 3H), 4.15 (t, J=7.3, 2H), 4.82 (br, 1H), 5.11 (s, 2H), 6.81 (d, J=8.6 Hz, 2H), 6.99 (d, J=8.6 Hz, 2H), 7.29 (d, J=8.4 Hz, 2H), 7.30-7.38 (m, 5H), 7.71 (d, J=8.4 Hz, 2H).

Example 7(6)

N-(4-(2-(1,2,3-triazol-1-yl)-ethyl)-phenyl)-4-benzyloxycarbonylaminopiperidine 1,2,3-triazole (3.4 ml, 58.6 mmol) was added to the N-(4-(2-tosyloxyethyl)phenyl)-4-benzyloxycarbonylaminopiperidine (3.0 g, 5.90 mmol) obtained in Example 7(5), followed by stirring at 90° C. for 2 hours. Methanol was added to the reaction mixture. The mixture was refluxed under heat for 1 hour, and then allowed to cool to room temperature. The precipitate was collected by filtration, thereby obtaining N-(4-(2-(1,2,3-triazol-1-yl)-ethyl)-phenyl)-4-benzyloxycarbonylaminopiperidine (1.3 g, 54%) as a white solid.

$^1$H-NMR (CDCl$_3$): δ (ppm) 1.50-1.65 (m, 2H), 2.07 (d, J=11.3 Hz, 2H), 2.84 (t, J=12.7 Hz, 2H), 3.12 (t, J=7.3 Hz, 2H), 3.54-3.67 (m, 3H), 4.57 (t, J=7.3, 2H), 4.69 (br, 1H), 5.11 (s, 2H), 6.84 (d, J=8.4 Hz, 2H), 6.96 (d, J=8.4 Hz, 2H), 7.30-7.38 (m, 6H), 7.61 (s, 1H).

Example 7(7)

N-(4-(2-(1,2,3-triazol-1-yl)-ethyl)-phenyl)-4-aminopiperidine

The N-(4-(2-(1,2,3-triazol-1-yl)-ethyl)-phenyl)-4-benzyloxycarbonylaminopiperidine (1.3 g, 50 mmol) obtained in Example 7 (6) was dissolved in methanol (13 ml) and THF (13 ml), and 10% palladium-carbon (hereinafter referred to as Pd—C) (130 mg) was added, followed by stirring at room temperature in an atmosphere of hydrogen gas for 24 hours. After the insoluble material was filtered with Celite, the solvent was evaporated from the filtrate under reduced pressure, thereby obtaining N-(4-(2-(1,2,3-triazol-1-yl)-ethyl)-phenyl)-4-aminopiperidine (870 mg, 99%) as a white solid.

¹H-NMR (DMSO): δ (ppm) 1.60-1.65 (m, 2H), 1.90-1.95 (m, 2H), 2.66-2.75 (m, 2H), 3.00-3.20 (m, 5H), 3.60-3.70 (m, 2H), 4.50-4.60 (m, 2H), 6.84 (d, J=8.4 Hz, 2H), 7.01 (d, J=8.4 Hz, 2H), 7.65 (s, 1H), 8.02 (s, 1H).

Example 7

4-((1-methylpyrrol-2-yl)-carbonyl)-N-(1-(4-(2-(1,2, 3-triazol-1-yl)-ethyl)-phenyl)-piperidin-4-yl)-1-piperazinecarboxamide (compound 7)

Following the procedure of Example 1(2), N-(4-(2-(1,2,3-triazol-1-yl)-ethyl)-phenyl)-4-aminopiperidine was used instead of 4-(4-aminopiperidin-1-yl)-benzoic acid tert-butyl ester, thereby obtaining 4-((1-methylpyrrol-2-yl)-carbonyl)-N-(1-(4-(2-(1,2,3-triazol-1-yl)-ethyl)-phenyl)-piperidin-4-yl)-1-piperazinecarboxamide (46%) as a milky-white solid.

¹H-NMR (CDCl₃): δ (ppm) 1.48-1.65 (m, 2H), 2.09 (d, J=12.0 Hz, 2H), 2.86 (d, J=11.0 Hz, 2H), 3.12 (t, J=7.0 Hz, 2H), 3.41-3.45 (m, 4H), 3.61 (d, J=13.0 Hz, 2H), 3.76-3.90 (m, 8H), 4.32 (d, J=7.3, 1H), 4.58 (t, J=7.3 Hz, 2H), 6.09 (dd, J=3.8, 2.7, 1H), 6.34 (dd, J=3.8, 1.4 Hz, 1H), 6.72 (dd, J=2.7, 1.4 Hz, 1H), 6.85 (d, J=8.9 Hz, 2H), 6.97 (d, J=8.9 Hz, 2H), 7.27 (s, 1H), 7.62 (s, 1H).

Example 8(1)

4-(4-tert-butoxycarbonylaminopiperidin-1-yl)-cinnamic acid ethyl ester 4-fluorobenzaldehyde (37 g, 0.30 mol) was dissolved in DMSO (300 ml), and potassium carbonate (124 g, 0.89 mol) and 4-tert-butoxycarbonylaminopiperidine (66 g, 0.33 mol) were added thereto, followed by stirring under heat at 120° C. for 12 hours. Triethyl phosphonoacetate (134 g, 0.60 mol) was added to the reaction mixture, further followed by stirring under heat for 2.5 hours. Water (900 ml) was added to the reaction mixture. After cooling to room temperature, the precipitate was collected by filtration and washed with water (300 ml) and hexane (300 ml), thereby obtaining 4-(4-tert-butoxycarbonylaminopiperidin-1-yl)-cinnamic acid ethyl ester (110 g, 99%) as a white solid.

¹H-NMR (CDCl₃): δ (ppm) 1.32 (t, J=7.1 Hz, 3H), 1.43-1.54 (m, 11H), 2.03-2.05 (m, 2H), 2.90-2.96 (m, 2H), 3.71-3.75 (m, 3H), 4.24 (q, J=7.1 Hz, 2H), 4.45 (brs, 1H), 6.26 (d, J=16 Hz, 1H), 6.87 (d, J=9.0 Hz, 2H), 7.41 (d, J=9.0 Hz, 2H), 7.60 (d, J=16 Hz, 1H)

Example 8(2)

4-(4-tert-butoxycarbonylaminopiperidin-1-yl)-dihydrocinnamic acid ethyl ester

The 4-(4-tert-butoxycarbonylaminopiperidin-1-yl)-cinnamic acid ethyl ester (126 g, 0.33 mol) obtained in Example 8 (1) was dissolved in ethanol (1 L), and 10% Pd—C (48.5 g) was added, followed by stirring in a hydrogen atmosphere for 18 hours. The insoluble material was filtered with Celite, and the filtrate was evaporated under reduced pressure, thereby obtaining 4-(4-tert-butoxycarbonylaminopiperidin-1-yl)-dihydrocinnamic acid ethyl ester (107 g, 85%) as a white solid.

¹H-NMR (CDCl₃): δ (ppm) 1.23 (t, J=7.1 Hz, 3H), 1.29-1.58 (m, 11H), 2.02-2.05 (m, 2H), 2.55-2.59 (m, 2H), 2.77-2.88 (m, 4H), 3.53-3.57 (m, 3H), 4.12 (q, J=7.1 Hz, 2H), 4.47 (brs, 1H), 6.86 (d, J=8.5 Hz, 2H), 7.08 (d, J=8.5 Hz, 2H)

Example 8 (3)

N-(4-(3-hydroxypropyl)phenyl)-4-tert-butoxycarbonylaminopiperidine

The 4-(4-tert-butoxycarbonylaminopiperidin-1-yl)-dihydrocinnamic acid ethyl ester (68 g, 0.18 mol) obtained in Example 8(2) was dissolved in toluene (1 L) and cooled to −78° C. A diisobutylaluminum hydride-hexane solution (607 ml, 0.6 mol) was added dropwise. After stirring for 1.5 hours, methanol (10 ml) and a saturated sodium chloride aqueous solution (550 ml) were added, followed by stirring for 3 hours. The insoluble material was filtered with Celite. The solvent was evaporated from the filtrate, and the obtained residue was dissolved in methanol (500 ml) and THF (250 ml). Sodium borohydride (6.9 g, 0.18 mol) was added thereto at 0° C. After stirring for 1 hour, a saturated ammonium chloride aqueous solution was added thereto, followed by extraction with chloroform and drying over magnesium sulfate. After the desiccant was filtered off, the solvent was evaporated, thereby obtaining N-(4-(3-hydroxypropyl)phenyl)-4-tert-butoxycarbonylaminopiperidine (60 g, 98%).

¹H-NMR (CDCl₃): δ (ppm) 1.45 (s, 9H), 1.50-1.61 (m, 2H), 1.82-1.89 (m, 2H), 2.02-2.05 (m, 2H), 2.60-2.64 (m, 2H), 2.77-2.83 (m, 2H), 3.48-3.66 (m, 5H), 4.48 (brs, 1H), 6.87 (d, J=8.5 Hz, 2H), 7.08 (d, J=8.5 Hz, 2H)

Example 8(4)

N-(4-(3-tosyloxypropyl)phenyl)-4-tert-butoxycarbonylaminopiperidine

Following the procedure of Example 7(5), N-(4-(3-hydroxypropyl)phenyl)-4-tert-butoxycarbonylaminopiperidine was used instead of N-(4-(2-hydroxyethyl)phenyl)-4-benzyloxycarbonylaminopiperidine, thereby obtaining N-(4-(3-tosyloxypropyl)phenyl)-4-tert-butoxycarbonylaminopiperidine (59%).

¹H-NMR (CDCl₃): δ (ppm) 1.46 (s, 9H), 1.49-1.52 (m, 2H), 1.87-1.94 (m, 2H), 2.02-2.05 (m, 2H), 2.45 (s, 3H), 2.56 (t, J=7.6 Hz, 2H), 2.76-2.82 (m, 2H), 3.50-3.55 (m, 3H), 4.02 (t, J=6.3 Hz, 2H), 4.47 (brs, 1H), 6.81 (d, J=8.4 Hz, 2H), 6.95 (d, J=8.4 Hz, 2H), 7.34 (d, J=8.2 Hz, 2H), 7.79 (d, J=8.2 Hz, 2H)

Example 8(5)

N-(4-(3-(1,2,4-triazol-1-yl)-propyl)-phenyl)-4-tert-butoxycarbonylaminopiperidine The N-(4-(3-tosyloxypropyl)phenyl)-4-tert-butoxycarbonylaminopiperidine (330 mg, 0.68 mmol) obtained in Example 8(4) was dissolved in a mixed solvent of acetonitrile (5 ml) and DMF (5 ml), and 1,2,4-triazole (54 mg, 0.81 mmol) and potassium carbonate (187 mg, 1.35 mmol) were added thereto, followed by stirring at 60° C. for 1 hour. After the reaction mixture was cooled to room temperature, water was added thereto, and the precipitate was collected by filtration, thereby obtaining N-(4-(3-(1,2,4-triazol-1-yl)-propyl)-phenyl)-4-tert-butoxycarbonylaminopiperidine (192 mg, 74%).

¹H-NMR (CDCl₃): δ (ppm) 1.45 (s, 9H), 1.51-1.61 (m, 2H), 2.01-2.04 (m, 2H), 2.15-2.23 (m, 2H), 2.52-2.57 (m, 2H), 2.77-2.82 (m, 2H), 3.56-3.59 (m, 3H), 4.15 (t, J=7.0 Hz, 2H), 4.94 (brs, 1H), 6.87 (d, J=8.5 Hz, 2H), 7.04 (d, J=8.5 Hz, 2H), 7.93 (s, 1H), 8.04 (s, 1H)

Example 8(6)

N-(4-(3-(1,2,4-triazol-1-yl)-propyl)-phenyl)-4-aminopiperidine

The N-(4-(3-(1,2,4-triazol-1-yl)-propyl)-phenyl)-4-tert-butoxycarbonylaminopiperidine (180 mg, 0.47 mmol) obtained in Example 8(5) was dissolved in trifluoroacetic acid (5 ml) at 0° C., followed by stirring at room temperature for 1 hour. The reaction mixture was evaporated under reduced pressure, and the obtained residue was purified using medium-pressure silica gel flash column chromatography (NH silica gel, methanol:chloroform=1:9), thereby obtaining N-(4-(3-(1,2,4-triazol-1-yl)-propyl)-phenyl)-4-aminopiperidine (127 mg, 95%).

$^1$H-NMR (DMSO-d$_6$): δ (ppm) 1.26-1.35 (m, 2H), 1.68-1.76 (m, 4H), 1.99-2.06 (m, 2H), 2.41-2.45 (m, 2H), 2.50-2.70 (m, 3H), 3.53-3.56 (m, 2H), 4.15 (t, J=7.0 Hz, 2H), 6.84 (d, J=8.8 Hz, 2H), 7.01 (d, J=8.8 Hz, 2H), 7.96 (s, 1H), 8.51 (s, 1H)

Example 8

4-((1-methylpyrrol-2-yl)-carbonyl)-N-(1-(4-(3-(1,2,4-triazol-1-yl)-propyl)-phenyl)-piperidin-4-yl)-1-piperazinecarboxamide (compound 8)

Following the procedure of Example 1(2), N-(4-(3-(1,2,4-triazol-1-yl)-propyl)-phenyl)-4-aminopiperidine was used instead of 4-(4-aminopiperidin-1-yl)-benzoic acid tert-butyl ester, thereby obtaining 4-((1-methylpyrrol-2-yl)-carbonyl)-N-(1-(4-(3-(1,2,4-triazol-1-yl)-propyl)-phenyl)-piperidin-4-yl)-1-piperazinecarboxamide (45%) as a white solid.

$^1$H-NMR (CDCl$_3$): δ (ppm) 1.53-1.57 (m, 2H), 2.06-2.10 (m, 2H), 2.18-2.22 (m, 2H), 2.54-2.57 (m, 2H), 2.84-2.87 (m, 2H), 3.43-3.45 (m, 4H), 3.60-3.63 (m, 2H), 3.75-3.90 (m, 8H), 4.12-4.16 (m, 2H), 4.38 (brs, 1H), 6.10 (d, J=3.0 Hz, 1H), 6.35 (s, 1H), 6.72 (s, 1H), 6.88 (d, J=8.4 Hz, 2H), 7.04 (d, J=8.4 Hz, 2H), 7.95 (s, 1H), 7.97 (s, 1H)

Example 9(1)

N-(4-(3-(3,5-dimethyl-1,2,4-triazol-1-yl)-propyl)-phenyl)-4-aminopiperidine

Following the procedures of Example 8(5) and Example 8(6), 3,5-dimethyl-1,2,4-triazole was used instead of 1,2,4-triazole, thereby obtaining N-(4-(3-(3,5-dimethyl-1,2,4-triazol-1-yl)-propyl)-phenyl)-4-aminopiperidine (52%) as a white solid.

$^1$H-NMR (CDCl$_3$): δ (ppm) 1.45-1.57 (m, 4H), 1.91-1.94 (m, 2H), 2.09-2.16 (m, 2H), 2.30 (s, 3H), 2.33 (s, 3H), 2.56 (t, J=7.5 Hz, 2H), 2.71-2.85 (m, 3H), 3.58-3.61 (m, 2H), 3.95 (t, J=7.2 Hz, 2H), 6.87 (d, J=8.7 Hz, 2H), 7.04 (d, J=8.7 Hz, 2H)

Example 9

4-((1-methylpyrrol-2-yl)-carbonyl)-N-(1-(4-(3-(3,5-dimethyl-1,2,4-triazol-1-yl)-propyl)-phenyl)-piperidin-4-yl)-1-piperazinecarboxamide (compound 9)

Following the procedure of Example 1(2), N-(4-(3-(3,5-dimethyl-1,2,4-triazol-1-yl)-propyl)-phenyl)-4-aminopiperidine was used instead of 4-(4-aminopiperidin-1-yl)-benzoic acid tert-butyl ester, thereby obtaining 4-((1-methylpyrrol-2-yl)-carbonyl)-N-(1-(4-(3-(3,5-dimethyl-1,2,4-triazol-1-yl)-propyl)-phenyl)-piperidin-4-yl)-1-piperazinecarboxamide (45%) as an amorphous solid.

$^1$H-NMR (CDCl$_3$): δ (ppm) 1.56-1.65 (m, 2H), 2.09-2.17 (m, 4H), 2.30 (s, 3H), 2.32 (s, 3H), 2.56 (t, J=7.4 Hz, 2H), 2.82-2.88 (m, 2H), 3.42-3.45 (m, 4H), 3.58-3.62 (m, 2H), 3.77-3.90 (m, 8H), 3.95 (t, J=7.0 Hz, 2H), 4.35 (d, J=7.3 Hz, 1H), 6.09-6.10 (m, 1H), 6.34 (d, J=3.9 Hz, 1H), 6.72 (s, 1H), 6.87 (d, J=8.5 Hz, 2H), 7.05 (d, J=8.5 Hz, 2H)

Example 10(1)

N-(4-(3-(1,2,3-triazol-1-yl)-propyl)-phenyl)-4-tert-butoxycarbonylaminopiperidine Following the procedure of Example 8(5), 1,2,3-triazole was used instead of 1,2,4-triazole, thereby obtaining N-(4-(3-(1,2,3-triazol-1-yl)-propyl)-phenyl)-4-tert-butoxycarbonylaminopiperidine (33%) as a white solid.

$^1$H-NMR (CDCl$_3$): δ (ppm) 1.46 (s, 9H), 1.51-1.57 (m, 2H), 2.03-2.06 (m, 2H), 2.18-2.26 (m, 2H), 2.57 (t, J=7.4 Hz, 2H), 2.79-2.84 (m, 2H), 4.36 (t, J=7.1 Hz, 2H), 4.48 (brs, 1H), 6.88 (d, J=8.3 Hz, 2H), 7.06 (d, J=8.3 Hz, 2H), 7.50 (s, 1H), 7.71 (s, 1H)

Example 10(2)

N-(4-(3-(1,2,3-triazol-1-yl)-propyl)-phenyl)-4-aminopiperidine

Following the procedure of Example 8(6), N-(4-(3-(1,2,3-triazol-1-yl)-propyl)-phenyl)-4-tert-butoxycarbonylaminopiperidine was used instead of N-(4-(3-(1,2,4-triazol-1-yl)-propyl)-phenyl)-4-tert-butoxycarbonylaminopiperidine, thereby obtaining N-(4-(3-(1,2,3-triazol-1-yl)-propyl)-phenyl)-4-aminopiperidine (83%) as an oil.

$^1$H-NMR (CDCl$_3$): δ (ppm) 1.45-1.61 (m, 4H), 1.90-1.94 (m, 2H), 2.18-2.26 (m, 2H), 2.57 (t, J=7.5 Hz, 2H), 2.72-2.84 (m, 3H), 3.59-3.63 (m, 2H), 4.37 (t, J=7.2 Hz, 2H), 6.88 (d, J=8.4 Hz, 2H), 7.05 (d, J=8.4 Hz, 2H), 7.50 (s, 1H), 7.70 (s, 1H)

Example 10

4-((1-methylpyrrol-2-yl)-carbonyl)-N-(1-(4-(3-(1,2,3-triazol-1-yl)-propyl)-phenyl)-piperidin-4-yl)-1-piperazinecarboxamide (compound 10)

Following the procedure of Example 1(2), N-(4-(3-(1,2,3-triazol-1-yl)-propyl)-phenyl)-4-aminopiperidine was used instead of 4-(4-aminopiperidin-1-yl)-benzoic acid tert-butyl ester, thereby obtaining 4-((1-methylpyrrol-2-yl)-carbonyl)-N-(1-(4-(3-(1,2,3-triazol-1-yl)-propyl)-phenyl)-piperidin-4-yl)-1-piperazinecarboxamide (42%) as a white solid.

$^1$H-NMR (CDCl$_3$): δ (ppm) 1.56-1.60 (m, 2H), 2.07-2.10 (m, 2H), 2.20-2.24 (m, 2H), 2.58 (t, J=7.1 Hz, 2H), 2.83-2.89 (m, 2H), 3.42-3.45 (m, 4H), 3.59-3.62 (m, 2H), 3.77-3.80 (m, 8H), 4.34-4.39 (m, 3H), 6.09-6.10 (m, 1H), 6.34-6.35 (m, 1H), 6.72 (s, 1H), 6.88 (d, J=8.5 Hz, 2H), 7.06 (d, J=8.5 Hz, 2H), 7.51 (s, 1H), 7.71 (s, 1H)

Example 11(1)

4-(4-tert-butoxycarbonylaminopiperidin-1-yl)-cinnamic acid

The 4-(4-tert-butoxycarbonylaminopiperidin-1-yl)-cinnamic acid ethyl ester (2.7 g, 7.2 mmol) obtained in Example 8(1) was dissolved in ethanol (40 ml), and a 4M sodium hydroxide aqueous solution (3.6 ml) was added thereto. The mixture was refluxed under heat for 12 hours. The reaction mixture was cooled to room temperature, and water (40 ml) was added thereto. The mixture was neutralized with 10% citric acid aqueous solution, and the precipitate was collected by filtration, thereby obtaining 4-(4-tert-butoxycarbonylaminopiperidin-1-yl)-cinnamic acid (1.9 g, 77%) as a white solid.

$^1$H-NMR (DMSO-$d_6$): δ (ppm) 1.34-1.43 (m, 11H), 1.75-1.78 (m, 2H), 2.80-2.86 (m, 2H), 3.32-3.48 (m, 1H), 3.76-3.79 (m, 2H), 6.24 (d, J=15.8 Hz, 1H), 6.83 (brs, 1H), 6.90 (d, J=8.8 Hz, 2H), 7.42-7.63 (m, 3H)

Example 11(2)

(3-(4-(4-tert-butoxycarbonylaminopiperidin-1-yl)-phenyl)-1-oxo-2-propen-1-yl)-morpholine The 4-(4-tert-butoxycarbonylaminopiperidin-1-yl)-cinnamic acid (870 mg, 2.5 mmol) obtained in Example 11(1) was dissolved in N,N-dimethylacetamide (hereinafter referred to as DMA) (15 ml), and HOBt (423 mg, 2.8 mmol), WSCD (530 mg, 2.8 mmol), morpholine (241 mg, 2.8 mmol) were added thereto, followed by stirring at 80° C. for 16 hours. After cooling to room temperature, water was added to the mixture, and the precipitate was collected by filtration, thereby obtaining (3-(4-(4-tert-butoxycarbonylaminopiperidin-1-yl)-phenyl)-1-oxo-2-propen-1-yl)-morpholine (836 mg, 80%) as a white solid.

$^1$H-NMR (CDCl$_3$): δ (ppm) 1.45 (s, 9H), 1.49-1.55 (m, 2H), 2.03-2.06 (m, 2H), 2.88-2.95 (m, 2H), 3.72 (brs, 11H), 4.47 (brs, 1H), 6.66 (d, J=15.4 Hz, 1H), 6.87 (d, J=8.8 Hz, 2H), 7.41 (d, J=8.8 Hz, 2H), 7.64 (d, J=15.4 Hz, 1H)

Example 11(3)

(3-(4-(4-aminopiperidin-1-yl)-phenyl)-1-oxo-2-propen-1-yl)-morpholine

Following the procedure of Example 8(6), (3-(4-(4-tert-butoxycarbonylaminopiperidin-1-yl)-phenyl)-1-oxo-2-propen-1-yl)-morpholine was used instead of N-(4-(3-(1,2,4-triazol-1-yl)-propyl)-phenyl)-4-tert-butoxycarbonylaminopiperidine, thereby obtaining (3-(4-(4-aminopiperidin-1-yl)-phenyl)-1-oxo-2-propen-1-yl)-morpholine (68%) as an oil.

$^1$H-NMR (CDCl$_3$): δ (ppm) 1.43-1.53 (m, 2H), 1.69 (brs, 2H), 1.92-1.95 (m, 2H), 2.83-2.92 (m, 3H), 3.71-3.77 (m, 10H), 6.66 (d, J=15.3 Hz, 1H), 6.87 (d, J=8.7 Hz, 2H), 7.42 (d, J=8.7 Hz, 2H), 7.64 (d, J=15.3 Hz, 1H)

Example 11

4-((1-methylpyrrol-2-yl)-carbonyl)-N-(1-(4-(3-morpholino-3-oxopropen-1-yl)-phenyl)-piperidin-4-yl)-1-piperazinecarboxamide (compound 11)

Following the procedure of Example 1(2), (3-(4-(4-aminopiperidin-1-yl)-phenyl)-1-oxo-2-propen-1-yl)-morpholine was used instead of 4-(4-aminopiperidin-1-yl)-benzoic acid tert-butyl ester, thereby obtaining 4-((1-methylpyrrol-2-yl)-carbonyl)-N-(1-(4-(3-morpholino-3-oxopropen-1-yl)-phenyl)-piperidin-4-yl)-1-piperazinecarboxamide (64%) as a white solid.

$^1$H-NMR (CDCl$_3$): δ (ppm) 1.47-1.57 (m, 2H), 2.07-2.10 (m, 2H), 2.93-2.98 (m, 2H), 3.42-3.44 (m, 4H), 3.72-3.90 (m, 18H), 4.30-4.32 (m, 1H), 6.09-6.10 (m, 1H), 6.33-6.35 (m, 1H), 6.66 (d, J=15.2 Hz, 1H), 6.71-6.72 (m, 1H), 6.88 (d, J=8.8 Hz, 2H), 7.42 (d, J=8.8 Hz, 2H), 7.64 (d, J=15.2 Hz, 1H)

Example 12

4-((1-methylpyrrol-2-yl)-carbonyl)-N-(1-(4-(3-morpholino-3-oxopropyl)-phenyl)-piperidin-4-yl)-1-piperazinecarboxamide (compound 12)

The 4-((1-methylpyrrol-2-yl)-carbonyl)-N-(1-(4-(3-morpholino-3-oxopropen-1-yl)-phenyl)-piperidin-4-yl)-1-piperazinecarboxamide (100 mg, 0.19 mmol) obtained in Example 11 was dissolved in THF (20 ml) and methanol (5 ml), and 10% Pd—C (39 mg) was added thereto, followed by stirring in a hydrogen atmosphere for 12 hours. After the insoluble material was filtered with Celite, the filtrate was evaporated under reduced pressure, thereby obtaining 4-((1-methylpyrrol-2-yl)-carbonyl)-N-(1-(4-(3-morpholino-3-oxopropyl)-phenyl)-piperidin-4-yl)-1-piperazinecarboxamide (84 mg, 84%) as a white solid.

$^1$H-NMR (CDCl$_3$): δ (ppm) 1.53-1.59 (m, 2H), 2.05-2.07 (m, 2H), 2.55-2.59 (m, 2H), 2.83-2.92 (m, 4H), 3.33-3.51 (m, 8H), 3.59-3.62 (m, 6H), 3.77-3.86 (m, 8H), 4.33 (d, J=7.3 Hz, 1H), 6.09 (dd, J=2.5, 3.7 Hz, 1H), 6.34 (dd, J=1.7, 3.7 Hz, 1H), 6.71-6.72 (m, 1H), 6.87 (d, J=8.8 Hz, 2H), 7.10 (d, J=8.8 Hz, 2H)

Example 13(1)

6-(4-aminopiperidin-1-yl)nicotinic acid ethyl ester 6-chloronicotinic acid ethyl ester (4.27 g, 23 mmol) was dissolved in DMF (30 ml), and potassium carbonate (4.77 g, 35 mmol) and 4-aminopiperidine (2.76 g, 28 mmol) were added thereto, followed by stirring at 80° C. for 3 hours and at 100° C. for 1 hour. After the reaction mixture was cooled to room temperature, water was added thereto, followed by extraction with ethyl acetate. The organic layer was washed with water and saturated sodium chloride, and then dried over anhydrous sodium sulfate. After the desiccant was filtered off, the solvent was evaporated under reduced pressure, thereby obtaining 6-(4-aminopiperidin-1-yl)nicotinic acid ethyl ester (4.17 g, 73%) as a pale brown oil.

$^1$H-NMR (CDCl$_3$): δ (ppm) 1.20-1.65 (m, 4H), 1.36 (t, J=7.1 Hz, 3H), 1.83-2.00 (m, 2H), 2.84-3.15 (m, 3H), 4.33 (q, J=7.1 Hz, 2H), 4.23-4.47 (m, 2H), 6.60 (dd, J=9.1, 0.6 Hz, 1H), 7.99 (dd, J=9.1, 2.4 Hz, 1H), 8.79 (dd, J=2.4, 0.6 Hz, 1H)

Example 13(2)

6-(4-(4-((1-methylpyrrol-2-yl)-carbonyl)-1-piperazinecarbamoyl)piperidin-1-yl)-nicotinic acid ethyl ester Following the procedure of Example 1(2), 6-(4-aminopiperidin-1-yl)nicotinic acid ethyl ester was used instead of 4-(4-aminopiperidin-1-yl)-benzoic acid tert-butyl ester, thereby obtaining 6-(4-(4-((1-methylpyrrol-2-yl)-carbonyl)-1-piperazinecarbamoyl)piperidin-1-yl)-nicotinic acid ethyl ester (61%) as a milky-white solid.

$^1$H-NMR (CDCl$_3$): δ (ppm) 1.27-1.50 (m, 2H), 1.36 (t, J=7.1 Hz, 3H), 1.97-2.18 (m, 2H), 3.00-3.17 (m, 2H), 3.31-3.48 (m, 4H), 3.65-3.85 (m, 4H), 3.79 (s, 3H), 3.87-4.06 (m, 1H), 4.33 (q, J=7.1 Hz, 2H), 4.28-4.52 (m, 2H), 6.06-6.15 (m, 1H), 6.29-6.40 (m, 1H), 6.61 (d, J=9.0 Hz, 1H), 6.67-6.77 (m, 1H), 8.01 (dd, J=9.0, 2.1 Hz, 1H), 8.79 (d, J=2.1 Hz, 1H)

Example 13

6-(4-(4-((1-methylpyrrol-2-yl)-carbonyl)-1-piperazinecarbamoyl)-piperidin-1-yl)-nicotinic acid (compound 13)

The 6-(4-(4-((1-methylpyrrol-2-yl)-carbonyl)-1-piperazinecarbamoyl)piperidin-1-yl)-nicotinic acid ethyl ester (234 mg, 0.5 mmol) obtained in Example 13(2) was dissolved in ethanol (1.5 ml) and THF (1.5 ml), and a 2M sodium hydroxide aqueous solution (1.4 ml, 2.8 mmol) was added thereto, followed by stirring at room temperature for 5 hours. The reaction mixture was neutralized with 2M aqueous hydrochloric acid, followed by extraction with methanol:chloroform (1:9). The organic layer was washed with water and saturated sodium chloride, and then dried over anhydrous sodium sulfate. After the desiccant was filtered off, the solvent was evaporated under reduced pressure, thereby obtaining 6-(4-(4-((1-methylpyrrol-2-yl)-carbonyl)-1-piperazinecarbamoyl)-piperidin-1-yl)-nicotinic acid (90%) as a milky-white solid.

$^1$H-NMR (CDCl$_3$): δ (ppm) 1.30-1.52 (m, 2H), 2.01-2.21 (m, 2H), 3.00-3.22 (m, 2H), 3.32-3.53 (m, 4H), 3.65-3.87 (m, 4H), 3.79 (s, 3H), 3.90-4.11 (m, 1H), 4.30-4.55 (m, 3H), 6.06-6.15 (m, 1H), 6.30-6.39 (m, 1H), 6.63 (d, J=9.2 Hz, 1H), 6.68-6.76 (m, 1H), 8.04 (dd, J=9.2, 2.4 Hz, 1H), 8.85 (d, J=2.4 Hz, 1H)

Example 14

4-((1-methylpyrrol-2-yl)-carbonyl)-N-(1-(5-(4-morpholinylcarbonyl)pyridin-2-yl)-piperidin-4-yl)-1-piperazinecarboxamide (compound 14)

The 6-(4-(4-((1-methylpyrrol-2-yl)-carbonyl)-1-piperazinecarbamoyl)-piperidin-1-yl)-nicotinic acid (132 mg, 0.3 mmol) obtained in Example 13 was dissolved in DMF (2.0 ml), and WSCD (69 mg, 0.36 mmol), HOBt (51 mg, 0.33 mmol), and morpholine (0.04 ml, 0.45 mmol) were added thereto, followed by stirring under heat at 60° C. for 16 hours. After cooling to room temperature, water was added to the reaction mixture, followed by extraction with ethyl acetate. The organic layer was washed with water and saturated sodium chloride, and then dried over anhydrous sodium sulfate. After the desiccant was filtered off, the residue obtained by evaporation under reduced pressure was purified using medium-pressure silica gel flash column chromatography (methanol:chloroform=1:50 to 1:15), thereby obtaining 4-((1-methylpyrrol-2-yl)-carbonyl)-N-(1-(5-(4-morpholinylcarbonyl)pyridin-2-yl)-piperidin-4-yl)-1-piperazinecarboxamide (24%) as a milky-white solid.

$^1$H-NMR (CDCl$_3$): δ (ppm) 1.32-1.54 (m, 2H), 2.00-2.19 (m, 2H), 2.96-3.15 (m, 2H), 3.34-3.50 (m, 4H), 3.55-4.07 (m, 13H), 3.79 (s, 3H), 4.26-4.48 (m, 3H), 6.04-6.15 (m, 1H), 6.30-6.42 (m, 1H), 6.66 (d, J=8.9 Hz, 1H), 6.68-6.79 (m, 1H), 7.60 (dd, J=8.9, 2.1 Hz, 1H), 8.26 (d, J=2.1 Hz, 1H)

Example 15(1)

4-(4-phenoxycarbonylaminopiperidin-1-yl)-benzoic acid tert-butyl ester

Phenyl chloroformate (7.83 g, 50.0 mmol) was dissolved in acetonitrile (100 ml), and a solution of the 4-(4-aminopiperidin-1-yl)-benzoic acid tert-butyl ester (13.82 g, 50.0 mmol) obtained in Example 1(1) in acetonitrile (50 ml) and DMA (50 ml) was added dropwise under ice-cooling. Triethylamine (7.0 ml, 50.0 mmol) was added thereto. After stirring at the same temperature for 2 hours, water was added thereto, and the precipitate was collected by filtration, thereby obtaining 4-(4-phenoxycarbonylaminopiperidin-1-yl)-benzoic acid tert-butyl ester (15.5 g, 78%) as a milky-white solid. The obtained 4-(4-phenoxycarbonylaminopiperidin-1-yl)-benzoic acid tert-butyl ester was used as is in the next reaction.

Example 15(2)

4-(4-((4-benzyloxycarbonyl)-1-piperazinecarbamoyl)piperidin-1-yl)-benzoic acid tert-butyl ester The 4-(4-phenoxycarbonylaminopiperidin-1-yl)-benzoic acid tert-butyl ester (13.88 g, 35.0 mmol) obtained in Example 15(1) was dissolved in acetonitrile (150 ml), and N-benzyloxycarbonylpiperazine (7.71 g, 35.0 mmol) and 1,8-diazabicyclo[5.4.0]undec-7-ene (6.6 ml, 42 mmol) were added thereto under ice-cooling, followed by stirring at room temperature for 19 hours. Then, water was added thereto, and the precipitate was collected by filtration, thereby obtaining 4-(4-((4-benzyloxycarbonyl)-1-piperazinecarbamoyl)piperidin-1-yl)-benzoic acid tert-butyl ester (16.1 g, 88%) as a milky-white solid.

$^1$H-NMR (CDCl$_3$): δ (ppm) 1.44-1.57 (m, 11H), 2.03-2.7 (m, 2H), 2.92-3.02 (m, 2H), 3.34-3.38 (m, 4H), 3.50-3.51 (m, 4H), 0.78-3.92 (m, 3H), 4.31 (d, J=7.4 Hz, 1H), 5.15 (s, 2H), 6.84 (dd, J=2.0, 7.1 Hz, 2H), 7.31-7.38 (m, 5H), 7.85 (dd, J=2.0, 7.1 Hz, 2H)

Example 15(3)

4-(4-((4-benzyloxycarbonyl)-1-piperazinecarbamoyl)piperidin-1-yl)-benzoic acid The 4-(4-((4-benzyloxycarbonyl)-1-piperazinecarbamoyl)piperidin-1-yl)-benzoic acid tert-butyl ester (5.23 g, 10.0 mmol) obtained in Example 15(2) was dissolved in formic acid (20 ml), followed by stirring at 60° C. for 3 hours. Water was added to the residue obtained by evaporation under reduced pressure, and the precipitate was collected by filtration, thereby obtaining 4-(4-((4-benzyloxycarbonyl)-1-piperazinecarbamoyl)piperidin-1-yl)-benzoic acid (4.75 g, quant.) as a milky-white solid.

$^1$H-NMR (DMSO-d$_6$): δ (ppm) 1.39-1.51 (m, 2H), 1.76-1.80 (m, 2H), 2.87-2.96 (m, 2H), 3.29-3.34 (m, 8H), 3.68-3.73 (m, 1H), 3.86-8.91 (m, 2H), 5.09 (s, 2H), 6.35 (d, J=7.6 Hz, 1H), 6.95 (d, J=8.9 Hz, 2H), 7.28-7.37 (m, 5H), 7.75 (d, J=8.9 Hz, 2H), 12.15 (brs, 1H)

Example 15(4)

4-benzyloxycarbonyl-N-(1-(4-(2-morpholinoethylcarbamoyl)-phenyl)-piperidin-4-yl)-1-piperazinecarboxamide The 4-(4-((4-benzyloxycarbonyl)-1-piperazinecarbamoyl)piperidin-1-yl)-benzoic acid (23.3 g, 50 mmol) obtained in Example 15(3) was dissolved in DMF (100 ml), and WSCD (10.5 g, 55 mmol), HOBt (8.04 g, 52.5 mmol), and 2-aminoethylmorpholine (7.9 ml, 60 mmol) were added thereto, followed by stirring under heat at 60° C. for 3 hours. After cooling to room temperature, a saturated sodium bicarbonate aqueous solution was added thereto, followed by extraction with ethyl acetate. The organic layer was washed with water and saturated sodium chloride, and then dried over anhydrous sodium sulfate. After the desiccant was filtered off, the solvent was evaporated under reduced pressure, thereby obtaining 4-benzyloxycarbonyl-N-(1-(4-(2-morpholinoethylcarbamoyl)-phenyl)-piperidin-4-yl)-1-piperazinecarboxamide (20.7 g, 72%) as a milky-white solid.

$^1$H-NMR (CDCl$_3$): δ (ppm) 1.46-1.57 (m, 2H), 2.04-2.07 (m, 2H), 2.48-2.51 (m, 4H), 2.58 (t, J=6.0 Hz, 2H), 2.90-3.00 (m, 2H), 3.34-3.38 (m, 4H), 3.50-3.55 (m, 6H), 3.70-3.80 (m, 7H), 4.43 (d, J=7.3 Hz, 1H), 5.14 (s, 2H), 6.63-6.66 (m, 1H), 6.89 (d, J=8.9 Hz, 2H), 7.31-7.38 (m, 5H), 7.67 (d, J=8.9 Hz, 2H)

Example 15(5)

N-(1-(4-(2-morpholinoethylcarbamoyl)phenyl)-piperidin-4-yl)-1-piperazinecarboxamide The 4-benzyloxycarbonyl-N-(1-(4-(2-morpholinoethylcarbamoyl)-phenyl)-piperidin-4-yl)-1-piperazinecarboxamide (14.5 g, 25.0 mmol) obtained in Example 15(4) was dissolved in methanol (80 ml) and THF (80 ml), and 10% Pd—C (3.0 g) was added thereto, followed by stirring at room temperature in a hydrogen atmosphere for 17 hours. To the reaction mixture, chloroform was added. After the insoluble material was filtered with Celite, the filtrate was evaporated under reduced pressure, thereby obtaining N-(1-(4-(2-morpholinoethylcarbamoyl)phenyl)-piperidin-4-yl)-1-piperazinecarboxamide (11.2 g, quant.) as a milky-white solid.

$^1$H-NMR (CDCl$_3$): δ (ppm) 1.50-1.60 (m, 2H), 2.02-2.05 (m, 2H) 2.45-2.61 (m, 7H), 2.82-3.00 (m, 6H), 3.31-3.35 (m, 4H), 3.49-3.56 (m, 2H), 3.70-3.90 (m, 7H), 4.88 (d, J=7.4 Hz, 1H), 6.85-6.86 (m, 1H), 6.90 (d, J=8.9 Hz, 2H), 7.69 (d, J=8.9 Hz, 2H)

Example 15

4-((1-ethylpyrrol-2-yl)-carbonyl)-N-(1-(4-(2-morpholinoethylcarbamoyl)phenyl)-piperidin-4-yl)-1-piperazinecarboxamide (compound 15)

1-ethylpyrrole-2-carboxylic acid (139 mg, 1.0 mmol) was dissolved in DMF (3.0 ml), and WSCD (230 mg, 1.2 mmol), HOBt (168 mg, 1.2 mmol), and N-(1-(4-(2-morpholinoethylcarbamoyl)phenyl)-piperidin-4-yl)-1-piperazinecarboxamide (400 mg, 0.9 mmol) obtained in Example 15(5) was added thereto, followed by stirring under heat at 80° C. for 14 hours. After the reaction mixture was allowed to cool to room temperature, a saturated sodium bicarbonate aqueous solution was added to the reaction mixture, followed by extraction with chloroform. The extract was washed with water and saturated sodium chloride, and then dried over anhydrous sodium sulfate. After the desiccant was filtered off, the residue obtained by evaporation under reduced pressure was purified using medium-pressure silica gel flash column chromatography (methanol:chloroform=1:30 to 1:10), thereby obtaining 4-((1-ethylpyrrol-2-yl)-carbonyl)-N-(1-(4-(2-morpholinoethylcarbamoyl)phenyl)-piperidin-4-yl)-1-piperazinecarboxamide (213 mg, 42%) as a milky-white solid.

$^1$H-NMR (CDCl$_3$): δ (ppm) 1.36 (t, J=7.3 Hz, 3H), 1.46-1.57 (m, 2H), 2.04-2.08 (m, 2H), 2.48-2.51 (m, 4H), 2.58 (t, J=6.0 Hz, 2H), 2.93-3.01 (m, 2H), 3.39-3.42 (m, 2H), 3.49-3.55 (m, 2H), 3.70-3.93 (m, 10H), 4.16 (q, J=7.3 Hz, 2H), 4.56 (brs, 1H), 6.10 (dd, J=2.6, 3.8 Hz, 1H), 6.30 (dd, J=1.7, 3.8 Hz, 1H), 6.79 (dd, J=1.7, 2.6 Hz, 1H), 6.90 (d, J=8.9 Hz, 2H), 7.67 (d, J=8.9 Hz, 2H)

Example 16

4-((1-ethylpyrrol-2-yl)-carbonyl)-N-(1-(4-(2-(1,2,3-triazol-1-yl)-ethyl)-phenyl)-piperidin-4-yl)-1-piperazinecarboxamide (compound 16)

Following the procedure of Example 1 (2), 1-((1-ethyl-1H-pyrrol-2-yl)carbonyl)piperazine hydrochloride was used instead of 1-((1-methyl-1H-pyrrol-2-yl)carbonyl)piperazine hydrochloride, thereby obtaining 4-((1-ethylpyrrol-2-yl)-carbonyl)-N-(1-(4-(2-(1,2,3-triazol-1-yl)-ethyl)-phenyl)-piperidin-4-yl)-1-piperazinecarboxamide (75%) as a white solid.

$^1$H-NMR (CDCl$_3$): δ (ppm) 1.38 (t, J=7.3 Hz, 3H), 1.51-1.57 (m, 2H), 2.06-2.09 (m, 2H), 2.80-2.90 (m, 2H), 3.12 (t, J=7.1 Hz, 2H), 3.40-3.44 (m, 4H), 3.58-3.63 (m, 2H), 3.76-3.90 (m, 5H), 4.18 (q, J=7.3 Hz, 2H), 4.38 (d, J=7.3 Hz, 1H), 7.58 (t, J=7.1 Hz, 2H), 6.10 (dd, J=2.6, 3.8 Hz, 1H), 6.32 (dd, J=1.7, 3.8 Hz, 1H), 6.79 (dd, J=1.7, 2.6 Hz, 1H), 6.85 (d, J=8.7 Hz, 2H), 6.97 (d, J=8.7 Hz, 2H), 7.28 (d, J=0.9 Hz, 1H), 7.62 (d, J=0.9 Hz, 1H)

Reference Examples

Method A

Following the procedure of Example 15, corresponding carboxylic acid was used instead of 1-ethylpyrrole-2-carboxylic acid, thereby obtaining the title compound.

Method B

N-(1-(4-(2-morpholinoethylcarbamoyl)phenyl)-piperidin-4-yl)-1-piperazinecarboxamide obtained in Example 15(5) was suspended in THF and chloroform, and triethylamine and corresponding acid chloride were added thereto, followed by stirring at room temperature. A saturated sodium bicarbonate aqueous solution was added to the reaction mixture, followed by extraction with chloroform. The extract was washed with water and saturated sodium chloride, and dried over anhydrous sodium sulfate. After the desiccant was filtered off, the residue obtained by evaporation under reduced pressure was purified using medium-pressure silica gel flash column chromatography, thereby obtaining the title compound.

Reference Example 1

4-((pyrrol-2-yl)-carbonyl)-N-(1-(4-(2-morpholinoethylcarbamoyl)phenyl)-piperidin-4-yl)-1-piperazinecarboxamide Method A, yield: 39%
$^1$H-NMR (CDCl$_3$): δ (ppm) 1.42-1.60 (m, 2H), 2.00-2.15 (m, 2H), 2.45-2.70 (m, 6H), 2.88-3.05 (m, 2H), 3.40-4.02 (m, 17H), 4.43 (d, J=6.9 Hz, 1H), 6.27 (s, 1H), 6.53 (s, 1H), 6.65 (brs, 1H), 6.80-7.05 (m, 3H), 7.67 (d, J=7.4 Hz, 2H), 9.55 (brs, 1H)

Reference Example 2

4-((3,5-dimethylpyrrol-2-yl)-carbonyl)-N-(1-(4-(2-morpholinoethylcarbamoyl)-phenyl)-piperidin-4-yl)-1-piperazinecarboxamide Method A, yield: 22%
$^1$H-NMR (DMSO-d$_6$): δ (ppm) 1.37-1.63 (m, 2H), 1.70-1.87 (m, 2H), 2.00 (s, 3H), 2.12 (s, 3H), 2.30-2.67 (m, 7H), 2.73-2.98 (m, 2H), 3.15-4.00 (m, 16H), 5.62 (s, 1H), 6.3 (m, 1H), 6.94 (d, J=8.9 Hz, 2H), 7.69 (d, J=8.9 Hz, 2H), 8.07 (brs, 1H), 10.73 (s, 1H)

Reference Example 3

4-((1-methylpyrrole-3-yl)-carbonyl)-N-(1-(4-(2-morpholinoethylcarbamoyl)-phenyl)-piperidin-4-yl)-1-piperazinecarboxamide Method A, yield: 38%
$^1$H-NMR (CDCl$_3$): δ (ppm) 1.40-1.62 (m, 2H), 1.98-2.15 (m, 2H), 2.42-2.67 (m, 6H), 2.88-3.07 (m, 2H), 3.33-4.05 (m, 17H), 3.66 (s, 3H), 4.53 (d, J=7.4 Hz, 1H), 6.22-6.30 (m, 1H), 6.50-6.73 (m, 2H), 6.90 (d, J=8.9 Hz, 2H), 6.95-7.03 (m, 1H), 7.67 (d, J=8.9 Hz, 2H)

Reference Example 4

4-((thiophen-2-yl)-carbonyl)-N-(1-(4-(2-morpholino-ethylcarbamoyl)-phenyl)-piperidin-4-yl)-1-piperazinecarboxamide Method A, yield: 58%
$^1$H-NMR (CDCl$_3$): δ (ppm) 1.40-1.62 (m, 2H), 1.97-2.15 (m, 2H), 2.38-2.65 (m, 6H), 2.88-3.05 (m, 2H), 3.35-4.04 (m, 17H), 4.56 (d, J=7.1 Hz, 1H), 6.64 (brs, 1H), 6.90 (d, J=8.9 Hz, 2H), 7.00-7.11 (m, 1H), 7.25-7.33 (m, 1H), 7.41-7.52 (m, 1H), 7.67 (d, J=8.9 Hz, 2H)

Reference Example 5

4-((thiophen-3-yl)-carbonyl)-N-(1-(4-(2-morpholino-ethylcarbamoyl)-phenyl)-piperidin-4-yl)-1-piperazinecarboxamide Method B, yield: 55%
$^1$H-NMR (CDCl$_3$): δ (ppm) 1.42-1.62 (m, 2H), 1.97-2.18 (m, 2H), 2.40-2.68 (m, 6H), 2.88-3.05 (m, 2H), 3.30-4.02 (m, 17H), 4.61 (d, J=6.9 Hz, 1H), 6.55-6.70 (m, 1H), 6.90 (d, J=8.9 Hz, 2H), 7.13-7.24 (m, 1H), 7.33-7.42 (m, 1H), 7.49-7.60 (m, 1H), 7.67 (d, J=8.9 Hz, 2H)

Reference Example 6

4-((furan-2-yl)-carbonyl)-N-(1-(4-(2-morpholinoethylcarbamoyl)-phenyl)-piperidin-4-yl)-1-piperazinecarboxamide Method B, yield: 71%
$^1$H-NMR (CDCl$_3$): δ (ppm) 1.40-1.63 (m, 2H), 1.97-2.15 (m, 2H), 2.37-2.67 (m, 6H), 2.86-3.08 (m, 2H), 3.35-4.00 (m, 17H), 4.68 (d, J=7.4 Hz, 1H), 6.50 (dd, J=3.5, 1.7 Hz, 1H), 6.60-6.77 (m, 1H), 6.89 (d, J=8.9 Hz, 2H), 7.03 (dd, J=3.5, 0.5 Hz, 1H), 7.43-7.56 (m, 1H), 7.67 (d, J=8.9 Hz, 2H)

Reference Example 7

4-((furan-3-yl)-carbonyl)-N-(1-(4-(2-morpholinoethylcarbamoyl)-phenyl)-piperidin-4-yl)-1-piperazinecarboxamide Method A, yield: 47%
$^1$H-NMR (CDCl$_3$): δ (ppm) 1.40-1.65 (m, 2H), 1.97-2.13 (m, 2H), 2.38-2.66 (m, 6H), 2.88-3.07 (m, 2H), 3.33-4.00 (m, 17H), 4.63 (d, J=7.4 Hz, 1H), 6.54 (dd, J=2.0, 0.8 Hz, 1H), 6.58-6.75 (m, 1H), 6.89 (d, J=9.1 Hz, 2H), 7.39-7.51 (m, 1H), 7.60-7.78 (m, 3H)

Reference Example 8

4-((isoxazol-5-yl)-carbonyl)-N-(1-(4-(2-morpholino-ethylcarbamoyl)-phenyl)-piperidin-4-yl)-1-piperazinecarboxamide Method B, yield: 43%
$^1$H-NMR (CDCl$_3$): δ (ppm) 1.38-1.63 (m, 2H), 1.92-2.13 (m, 2H), 2.39-2.68 (m, 6H), 2.85-3.08 (m, 2H), 3.38-4.03 (m, 17H), 4.77 (d, J=7.4 Hz, 1H), 6.58-6.75 (m, 1H), 6.81 (d, J=1.8 Hz, 1H), 6.89 (d, J=8.9 Hz, 2H), 7.66 (d, J=8.9 Hz, 2H), 8.33 (d, J=1.8 Hz, 1H)

Reference Example 9

4-((1-methylimidazol-2-yl)-carbonyl)-N-(1-(4-(2-morpholinoethylcarbamoyl)-phenyl)-piperidin-4-yl)-1-piperazinecarboxamide Method A, yield: 46%
$^1$H-NMR (CDCl$_3$): δ (ppm) 1.40-1.63 (m, 2H), 1.95-2.18 (m, 2H), 2.40-2.70 (m, 6H), 2.85-3.10 (m, 2H), 3.35-4.28 (m, 17H), 3.89 (s, 3H), 4.50 (d, J=7.4 Hz, 1H), 6.69 (brs, 1H), 6.90 (d, J=8.9 Hz, 2H), 6.96 (d, J=1.0 Hz, 1H), 7.04 (d, J=1.0 Hz, 1H), 7.68 (d, J=8.9 Hz, 2H)

Reference Example 10

4-cyclopentylcarbonyl-N-(1-(4-(2-morpholinoethylcarbamoyl)-phenyl)-piperidin-4-yl)-1-piperazinecarboxamide Method B, yield: 65%
$^1$H-NMR (CDCl$_3$): δ (ppm) 1.40-1.92 (m, 11H), 1.99-2.15 (m, 2H), 2.42-2.68 (m, 6H), 2.88-3.10 (m, 2H), 3.25-3.98 (m, 17H), 4.40 (d, J=7.4 Hz, 1H), 6.58-6.75 (m, 1H), 6.90 (d, J=8.9 Hz, 2H), 7.68 (d, J=8.9 Hz, 2H)

Reference Example 11

4-benzoyl-N-(1-(4-(2-morpholinoethylcarbamoyl)-phenyl)-piperidin-4-yl)-1-piperazinecarboxamide Method A, yield: 13%
$^1$H-NMR (CDCl$_3$): δ (ppm) 1.39-1.63 (m, 2H), 2.00-2.15 (m, 2H), 2.42-2.67 (m, 6H), 2.87-3.06 (m, 2H), 3.28-4.05 (m, 17H), 4.51 (d, J=7.4 Hz, 1H), 6.55-6.72 (m, 1H), 6.90 (d, J=8.9 Hz, 2H), 7.30-7.53 (m, 5H), 7.67 (d, J=8.9 Hz, 2H)

Reference Example 12

4-(3-fluorobenzoyl)-piperazine-1-carboxylic acid-(6-bromobenzothiazol-2-yl)-amide

Reference Example 13

4-(3-fluorobenzoyl)-piperazine-1-carboxylic acid-(5,6-dimethylbenzothiazol-2-yl)-amide

Reference Example 14

4-(3-fluorobenzoyl)-piperazine-1-carboxylic acid-(6-methylbenzothiazol-2-yl)-amide

Reference Example 15

4-(3-fluorobenzoyl)-piperazine-1-carboxylic acid-(6-methoxybenzothiazol-2-yl)-amide

Reference Example 16

4-(3-fluorobenzoyl)-piperazine-1-carboxylic acid-(6-chlorobenzothiazol-2-yl)-amide

Reference Example 17

4-(6-fluoropyridine-2-carbonyl)-piperazine-1-carboxylic acid-(4-trifluoromethylphenyl)-amide Reference Examples 12 to 17 were synthesized according to the procedure of the method disclosed in International Publication WO2008-122787.

Reference Example 18

N-methoxy-N-methyl-4-(5-benzoylbenzimidazol-2-yl-3,5-dimethylpyrrol-2-carboxamide The synthesis was carried out according to the method disclosed in International Publication WO2007-007778.

Test Examples

Test Example 1

Hematopoietic Prostaglandin D Synthase (H-PGDS) Inhibiting Action

The test was carried out according to the method of Urade, Y. et al. (J. Biol. Chem., 262, 3820-3825, (1987)). More specifically, the reaction mixture (49 μL) containing 100 mM Tris-HCl (pH 8.0), 1 mM reduced glutathione, 0.1 mg/mL γ-globulin, and human H-PGDS (q.s.), and a compound (final concentration: 0.01-100 μM) was preincubated at 25° C. for 5 minutes. A DMSO solution (final concentration: 1%) was added to the solvent control group. Subsequently, 1 μL of [$^{14}$C] prostaglandin H2 (final concentration: 10 μM) was added to start the reaction. One minute after the start of the reaction, 250 μL of a reaction stop solution (diethylether/methanol/1 M citric acid (30/4/1) at a temperature of −20° C. was added to stop the reaction. After the reaction was stopped, 50 μL of the upper-layer portion (organic solvent layer) was applied to a TLC plate and developed at −20° C. for 45 minutes (developing solvent: diethylether/methanol/acetic acid (90/2/1)). After drying the TLC plate, the TLC plate was exposed to an imaging plate for 1 to 24 hours, and the radioactivity corresponding to prostaglandin D2 (PGD2) was analyzed using an image analyzer (produced by Fujifilm Corporation). The area (%) occupied by the PGD2 band per lane was calculated to determine the inhibition rate (%) of each Example compound at 0.1 μM relative to the control group in each experiment, as well as the inhibition concentration at 50% (IC50 value, nM) relative to H-PGDS. Tables 1 and 2 show the results.

TABLE 1

| Compound Number | X | R1 | R2 | Inhibition Rate (%) 0.1 μM | IC50 (nM) |
|---|---|---|---|---|---|
| 1 | CH | Me | 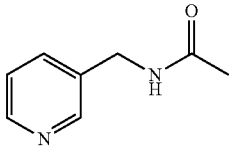 | 57.7 | 67 |
| 2 | CH | Me | | 55.2 | |
| 3 | CH | Me | 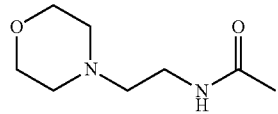 | 69.1 | 27 |

TABLE 1-continued
| | | | | | |
|---|---|---|---|---|---|
| 4 | CH | Me | 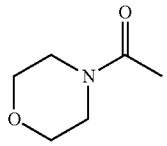 | 69.8 | 31 |
| 5 | CH | Me | 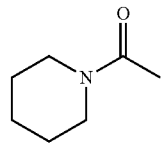 | 67.6 | 41 |
| 6 | CH | Me | 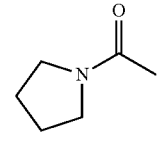 | 63.0 | 52 |
| 7 | CH | Me | 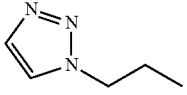 | 75.0 | 15 |
| 8 | CH | Me | 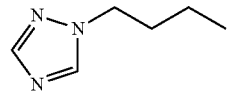 | 60.6 | |
| 9 | CH | Me | 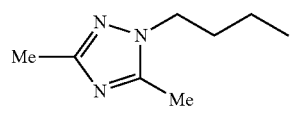 | 54.2 | 61 |
| 10 | CH | Me | 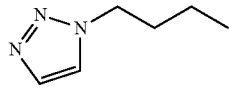 | 74.8 | 27 |
| 11 | CH | Me | 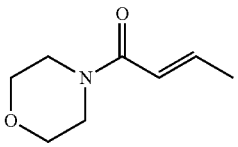 | 66.7 | |
| 12 | CH | Me | 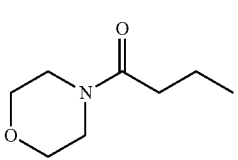 | 53.6 | |
| 13 | N | Me |  | 52.8 | |
| 14 | N | Me | 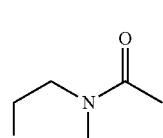 | 57.2 | |
| 15 | CH | Et | 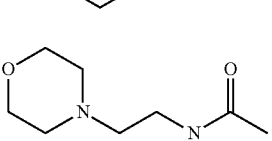 | 69.9 | 39 |

TABLE 1-continued
| 16 | CH | Et | 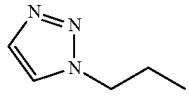 | | 68.4 | |
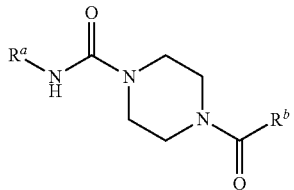
| Compound Number | $R^a$ | $R^b$ | Inhibition Rate (%) 0.1 μM | IC50 (nM) |
|---|---|---|---|---|
| Reference Example 1 | 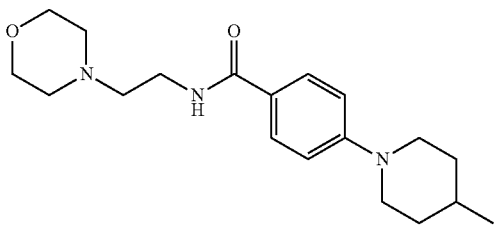 | 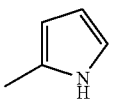 | | 334 |
| Reference Example 2 | 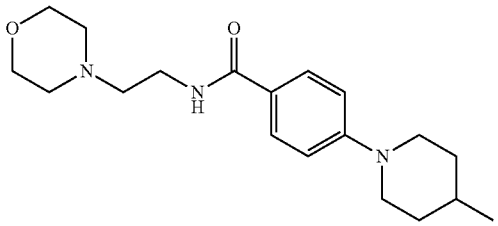 | 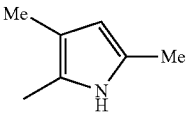 | | >1000 |
| Reference Example 3 | 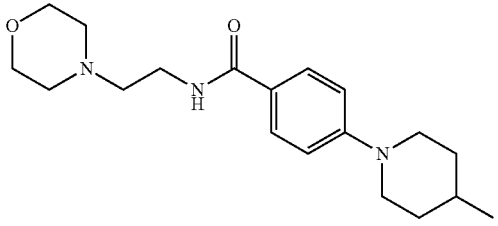 | 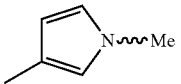 | | >1000 |
| Reference Example 4 | 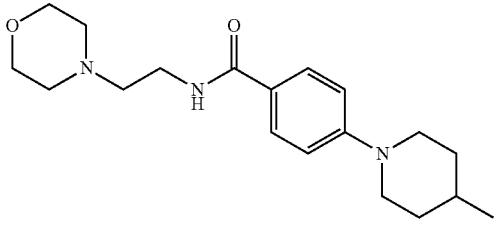 | 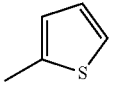 | 29.2 | 201 |
| Reference Example 5 | 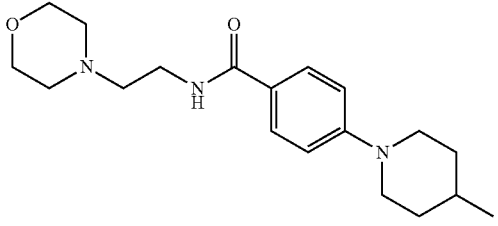 | 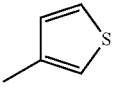 | | 327 |

TABLE 1-continued
| | | | | |
|---|---|---|---|---|
| Reference Example 6 | 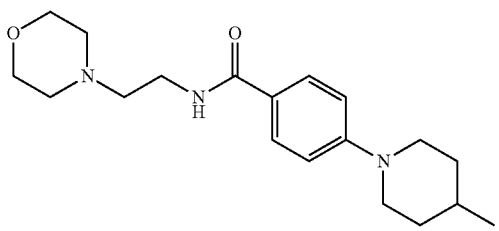 | 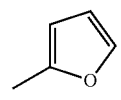 | | 445 |
| Reference Example 7 | 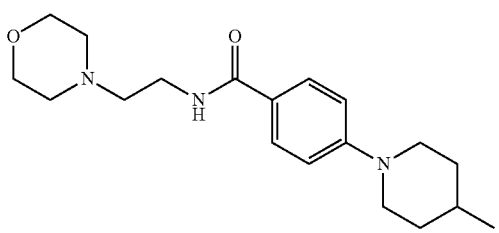 | 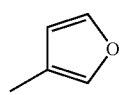 | | >1000 |
| Reference Example 8 | 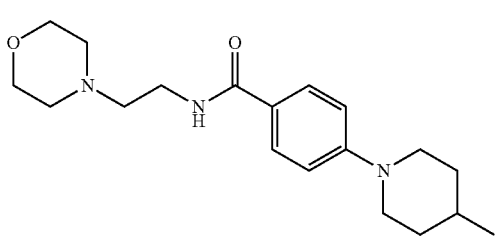 | 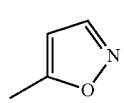 | | >1000 |
| Reference Example 9 | 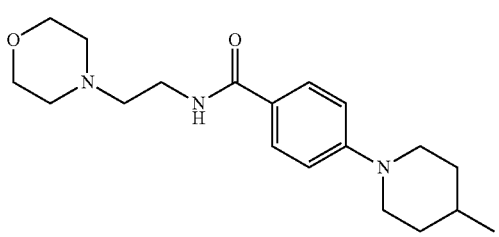 | 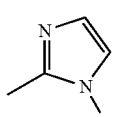 | | >1000 |
| Reference Example 10 | 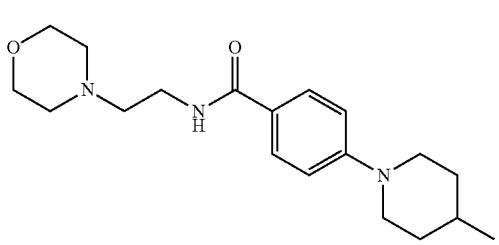 | 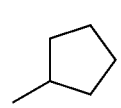 | | >1000 |
| Reference Example 11 | 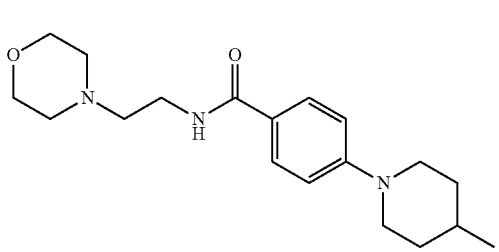 | 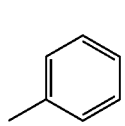 | 30.0 | 249 |
| Reference Example 12 | 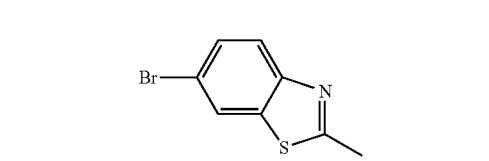 | 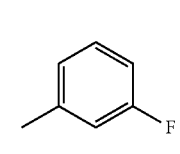 | 45.1 | 106 |

TABLE 1-continued

| | | | | |
|---|---|---|---|---|
| Reference Example 13 | 5,6-dimethyl-2-methyl-benzothiazole | 3-fluorobenzoyl | 31.6 | 222 |
| Reference Example 14 | 6-methyl-2-methyl-benzothiazole | 3-fluorobenzoyl | 27.9 | 260 |
| Reference Example 15 | 6-methoxy-2-methyl-benzothiazole | 3-fluorobenzoyl | 20.9 | 318 |
| Reference Example 16 | 6-chloro-2-methyl-benzothiazole | 3-fluorobenzoyl | 33.8 | 204 |
| Reference Example 17 | 4-(trifluoromethyl)toluene | 6-fluoropyridine-2-carbonyl | 1.8 | 5817 |

Reference Examples 1 to 11 are compounds in which the (N-alkylpyrrol-2-yl)-carbonyl group, which characterizes the compounds of the present invention, is replaced by another substituent such as a heterocyclic ring. As shown in Table 1, the piperazine compound having an (N-alkylpyrrol-2-yl)-carbonyl group as in the compounds of the present invention showed a strong H-PGDS inhibitory effect, whereas Reference Examples 1 to 11 showed little inhibitory effect.

Further, Reference Examples 12 to 16 are compounds having a structure similar to that of the compounds of the present invention, i.e., a structure comprising a fluorobenzoyl group and an aminocarbonyl group, and having a high GST2 inhibitory activity (Range A). Reference Example 17 is a compound comprising a fluoropyridinecarbonyl group and an aminocarbonyl group, and is effective against metabolic syndrome in mice. All of these compounds are disclosed in Patent Literature 3.

The compounds of the present invention clearly showed a stronger H-PGDS inhibitory effect than Reference Examples 12 to 17.

Test Example 2

PGD2 Production Inhibiting Action in the Nasal Cavities of Guinea Pigs with Antigen-Induced Rhinitis A physiological saline solution containing 1 mg/mL of ovalbumin was subcutaneously injected into the back of 5-week-old male Std: Hartley guinea pigs in an amount of 1 mL/body for active sensitization (initial sensitization). One week and two weeks after initial sensitization, 20 µL of a physiological saline solution containing 10 mg/mL of ovalbumin was instilled into each nasal cavity using a micropipette (sensitization by nasal administration). Three weeks after initial sensitization, 20 µL of a physiological saline solution containing 10 mg/mL of ovalbumin was instilled into each nasal cavity using a micropipette to induce a rhinitis reaction.

30 minutes after the induction of a rhinitis reaction, the nasal cavities were washed under pentobarbital sodium anesthesia. A nasal cavity washing liquid (phosphate buffered saline containing 3 mM of EDTA and 10 µM of indomethacin) was flushed using a Peristaltic Pump (Gilson, Inc.) in the direction from the trachea to the upper respiratory tract at a flow rate of 1 mL/min, and the liquid flowing out from the nasal cavities was collected for 1 minute. The collected liquid was centrifuged to separate the supernatant as the nasal cavity washing fluid. The concentration of PGD2 in the nasal cavity washing fluid was determined using an EIA kit (Prostaglandin D2-MOX EIA kit, Cayman Chemical).

The test compound (30 mg/kg) was orally administered 1 hour before induction of a rhinitis reaction. A formula to calculate the rate of decrease in PGD2 in the nasal cavity washing fluid is shown below.

Rate (%) of decrease in PGD2 in the nasal cavity washing fluid={(PGD2 concentration in the control group−PGD2 concentration in the compound-administered group)÷(PGD2 concentration in the control group−PGD2 concentration in the normal group)}×100

8 or more cases were obtained from each group to determine whether expression of the PGD2 production inhibiting action occurred, and the PGD2 concentration in the nasal cavity washing fluid was compared between the control group and each compound-administered group. Table 2 shows the results. When the significance level was below 0.05, the action was considered to be present and indicated by a symbol (*) in the table. Reference Example 18, known as an H-PGDS inhibitor, was used as a positive control substance.

TABLE 2

| Compounds | Rate (%) of decrease in PGD2 in the nasal cavity washing fluid |
|---|---|
| Example 5 | 88.0* |
| Reference Example 18 | 77.0* |
| Reference Example 12 | 7.9 |
| Reference Example 13 | 3.9 |
| Reference Example 14 | 26.6 |
| Reference Example 15 | −27.4 |
| Reference Example 16 | −38.1 |
| Reference Example 17 | 31.0 |

According to the results in Table 2, the compound of the present invention indicated a rate of decrease in the PGD2 concentration similar to that of Reference Example 18 (these compounds have significant differences). In contrast, Reference Examples 12 to 17 disclosed in Patent Literature 3 did not show a significant decrease in the PGD2 concentration.

The invention claimed is:

1. A piperazine compound represented by Formula (I) or a salt thereof,

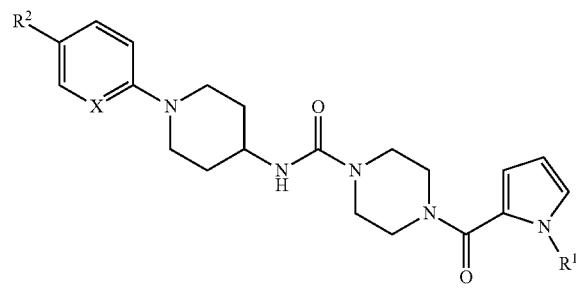

(I)

wherein
X represents CH or an N atom;
$R^1$ represents $C_{1-6}$ alkyl;
$R^2$ represents:
  $C_{1-6}$ alkyl optionally substituted with at least one of halogen, hydroxyl, cyano, nitro, alkyl, halogenoalkyl, cycloalkyl, cycloalkyl-alkyl, aralkyl, alkenyl, alkynyl, alkoxy, halogenoalkoxy, cycloalkoxy, cycloalkyl-alkoxy, aralkyloxy, alkylthio, cycloalkyl-alkylthio, amino, mono- or di-alkylamino, cycloalkyl-alkylamino, acyl, acyloxy, oxo, carboxyl, alkoxycarbonyl, aralkyloxycarbonyl, carbamoyl, saturated or unsaturated heterocyclic group, aromatic hydrocarbon, or saturated heterocycloxy group, or
  $C_{2-6}$ alkenyl optionally substituted with at least one of halogen, hydroxyl, cyano, nitro, alkyl, halogenoalkyl, cycloalkyl, cycloalkyl-alkyl, aralkyl, alkenyl, alkynyl, alkoxy, halogenoalkoxy, cycloalkoxy, cycloalkyl-alkoxy, aralkyloxy, alkylthio, cycloalkyl-alkylthio, amino, mono- or di-alkylamino, cycloalkyl-alkylamino, acyl, acyloxy, oxo, carboxyl, alkoxycarbonyl, aralkyloxycarbonyl, carbamoyl, saturated or unsaturated heterocyclic group, aromatic hydrocarbon, or saturated heterocycloxy group, or
  —(C=O)—N($R^3$)($R^4$), or
  —(C=O)—$OR^5$,
$R^3$ and $R^4$ are the same or different, and each represents:
  hydrogen or
  $C_{1-6}$ alkyl optionally substituted with at least one of halogen, hydroxyl, cyano, nitro, alkyl, halogenoalkyl, cycloalkyl, cycloalkyl-alkyl, aralkyl, alkenyl, alkynyl, alkoxy, halogenoalkoxy, cycloalkoxy, cycloalkyl-alkoxy, aralkyloxy, alkylthio, cycloalkyl-alkylthio, amino, mono- or di-alkylamino, cycloalkyl-alkylamino, acyl, acyloxy, oxo, carboxyl, alkoxycarbonyl, aralkyloxycarbonyl, carbamoyl, saturated or unsaturated heterocyclic group, aromatic hydrocarbon, or saturated heterocycloxy group; or
  $R^3$ and $R^4$ taken together with a nitrogen atom to which $R^3$ and $R^4$ are attached, form a saturated heterocyclic group; and
$R^5$ represents:
  hydrogen or
  $C_{1-6}$ alkyl optionally substituted with at least one of halogen, hydroxyl, cyano, nitro, alkyl, halogenoalkyl, cycloalkyl, cycloalkyl-alkyl, aralkyl, alkenyl, alkynyl, alkoxy, halogenoalkoxy, cycloalkoxy, cycloalkyl-alkoxy, aralkyloxy, alkylthio, cycloalkyl-alkylthio, amino, mono- or di-alkylamino, cycloalkyl-alkylamino, acyl, acyloxy, oxo, carboxyl, alkoxycarbonyl, aralkyloxycarbonyl, carbamoyl, saturated or unsaturated heterocyclic group, aromatic hydrocarbon, or saturated heterocycloxy group or
  Aralkyl
    wherein said carbamoyl group is selected from $CONH_2$, (mono- or di-alkyl)carbamoyl, (mono- or di-aryl)carbamoyl, (N-alkyl-N-aryl)carbamoyl, pyrrolidinocarbamoyl, piperidinocarbamoyl, piperazinocarbamoyl, or morpholinocarbamoyl.

2. The piperazine compound according to claim 1 or a salt thereof, wherein
X represents CH or an N atom;
$R^1$ represents methyl or ethyl;
$R^2$ represents:
  $C_{1-3}$ alkyl optionally substituted with at least one carbamoyl or unsaturated heterocyclic group, propenyl optionally substituted with at least one carbamoyl group, or
  —(C=O)—N($R^3$)($R^4$), or
  —(C=O)—$OR^5$;
one of $R^3$ and $R^4$ represents hydrogen and the other represents:
  $C_{1-6}$ alkyl optionally substituted with at least one saturated or unsaturated heterocyclic group; or
$R^3$ and $R^4$, taken together with a nitrogen atom to which $R^3$ and $R^4$ are attached, form pyrrolidinyl, piperidinyl, piperazinyl, and morpholino; and
$R^5$ represents hydrogen, methyl, ethyl, tert-butyl, or benzyl;
wherein said carbamoyl group is selected from $CONH_2$, (mono- or di-alkyl)carbamoyl, (mono- or di-aryl)carbamoyl, (N-alkyl-N-aryl)carbamoyl, pyrrolidinocarbamoyl, piperidinocarbamoyl, piperazinocarbamoyl, or morpholinocarbamoyl.

3. A piperazine compound represented by Formula (I) or a salt thereof, wherein

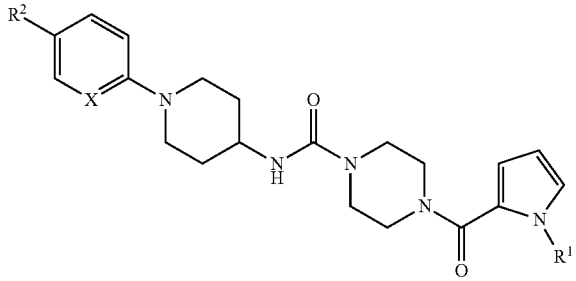

(I)

X represents CH or an N atom;
R¹ represents methyl;
R² represents $C_{1-3}$ alkyl that may have as a substituent any one of:
 a morpholinocarbamoyl group or
 a triazolyl group which may have one or two $C_{1-6}$ alkyl groups as substituents; or
 —(C=O)—N(R³)(R⁴), or
 —(C=O)—OR⁵;
one of R³ and R⁴ represents hydrogen and the other represents:
 $C_{1-3}$ alkyl that may have at least one morpholino or pyridyl group as a substituent; or
 R³ and R⁴, taken together with a nitrogen atom to which R³ and R⁴ are attached, form morpholino; and
R⁵ represents hydrogen.

4. The piperazine compound according to claim 3 or a salt thereof, wherein
X represents CH;
R¹ represents methyl;
R² represents linear $C_{1-3}$ alkyl that may have as a substituent any one of 1,2,3-triazolyl, 1,2,4-triazolyl, 3,5-dimethyl-1,2,4-triazolyl, —(C=O)—N(R³)(R⁴), or —(C=O)—OR⁵;
R³ and R⁴, taken together with a nitrogen atom to which R³ and R⁴ are attached, form morpholino; and
R⁵ represents hydrogen.

5. The piperazine compound or a salt thereof selected from the group consisting of:
 4-(4-(4-((1-methylpyrrol-2-yl)-carbonyl)-1-piperazinecarbamoyl)piperidin-1-yl)-benzoic acid,
 4-((1-methylpyrrol-2-yl)-carbonyl)-N-(1-(4-(pyridin-3-ylmethylcarbamoyl)phenyl)-piperidin-4-yl)-1-piperazinecarboxamide,
 4-((1-methylpyrrol-2-yl)-carbonyl)-N-(1-(4-(2-morpholinoethylcarbamoyl)-phenyl)-piperidin-4-yl)-1-piperazinecarboxamide,
 4-((1-methylpyrrol-2-yl)-carbonyl)-N-(1-(4-(4-morpholinylcarbonyl)phenyl)-piperidin-4-yl)-1-piperazinecarboxamide,
 4-((1-methylpyrrol-2-yl)-carbonyl)-N-(1-(4-(1-piperidinylcarbonyl)phenyl)-piperidin-4-yl)-1-piperazinecarboxamide,
 4-((1-methylpyrrol-2-yl)-carbonyl)-N-(1-(4-(1-pyrrolidinylcarbonyl)phenyl)-piperidin-4-yl)-1-piperazinecarboxamide,
 4-((1-methylpyrrol-2-yl)-carbonyl)-N-(1-(4-(2-(1,2,3-triazol-1-yl)-ethyl)-phenyl)-piperidin-4-yl)-1-piperazinecarboxamide,
 4-((1-methylpyrrol-2-yl)-carbonyl)-N-(1-(4-(3-(1,2,4-triazol-1-yl)-propyl)-phenyl)-piperidin-4-yl)-1-piperazinecarboxamide,
 4-((1-methylpyrrol-2-yl)-carbonyl)-N-(1-(4-(3-(3,5-dimethyl-1,2,4-triazol-1-yl)-propyl)-phenyl)-piperidin-4-yl)-1-piperazinecarboxamide,
 4-((1-methylpyrrol-2-yl)-carbonyl)-N-(1-(4-(3-(1,2,3-triazol-1-yl)-propyl)-phenyl)-piperidin-4-yl)-1-piperazinecarboxamide,
 4-((1-methylpyrrol-2-yl)-carbonyl)-N-(1-(4-(3-morpholino-3-oxopropen-1-yl)-phenyl)-piperidin-4-yl)-1-piperazinecarboxamide,
 4-((1-methylpyrrol-2-yl)-carbonyl)-N-(1-(4-(3-morpholino-3-oxopropyl)-phenyl)-piperidin-4-yl)-1-piperazinecarboxamide,
 6-(4-(4-((1-methylpyrrol-2-yl)-carbonyl)-1-piperazinecarbamoyl)piperidin-1-yl)-nicotinic acid,
 4-((1-methylpyrrol-2-yl)-carbonyl)-N-(1-(5-(4-morpholinylcarbonyl)pyridin-2-yl)-piperidin-4-yl)-1-piperazinecarboxamide,
 4-((1-ethylpyrrol-2-yl)-carbonyl)-N-(1-(4-(2-morpholinoethylcarbamoyl)phenyl)-piperidin-4-yl)-1-piperazinecarboxamide, and
 4-((1-ethylpyrrol-2-yl)-carbonyl)-N-(1-(4-(2-(1,2,3-triazol-1-yl)-ethyl)-phenyl)-piperidin-4-yl)-1-piperazinecarboxamide.

6. A pharmaceutical composition comprising an effective amount of at least one of the compounds according to claim 1 or pharmaceutically acceptable salts thereof, and a pharmaceutically acceptable carrier.

7. A method for treating allergic rhinitis, comprising administering to a patient in need of such treatment an effective amount of a piperazine compound represented by Formula (I) or a salt thereof

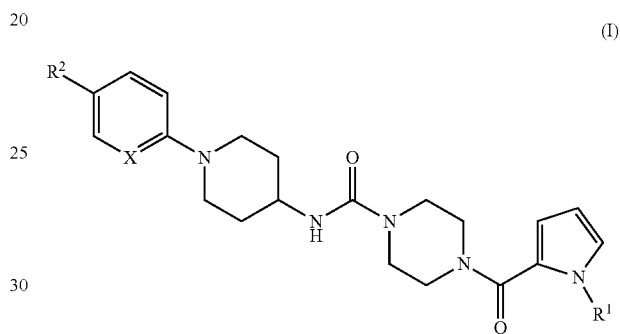

wherein
X represents CH or an N atom;
R¹ represents $C_{1-6}$ alkyl;
R² represents:
 $C_{1-6}$ alkyl optionally substituted with at least one of halogen, hydroxyl, cyano, nitro, alkyl, halogenoalkyl, cycloalkyl, cycloalkyl-alkyl, aralkyl, alkenyl, alkynyl, alkoxy, halogenoalkoxy, cycloalkoxy, cycloalkyl-alkoxy, aralkyloxy, alkylthio, cycloalkyl-alkylthio, amino, mono- or di-alkylamino, cycloalkyl-alkylamino, acyl, acyloxy, oxo, carboxyl, alkoxycarbonyl, aralkyloxycarbonyl, carbamoyl, saturated or unsaturated heterocyclic group, aromatic hydrocarbon, or saturated heterocycloxy group, or
 $C_{2-6}$ alkenyl optionally substituted with at least one of halogen, hydroxyl, cyano, nitro, alkyl, halogenoalkyl, cycloalkyl, cycloalkyl-alkyl, aralkyl, alkenyl, alkynyl, alkoxy, halogenoalkoxy, cycloalkoxy, cycloalkyl-alkoxy, aralkyloxy, alkylthio, cycloalkyl-alkylthio, amino, mono- or di-alkylamino, cycloalkyl-alkylamino, acyl, acyloxy, oxo, carboxyl, alkoxycarbonyl, aralkyloxycarbonyl, carbamoyl, saturated or unsaturated heterocyclic group aromatic hydrocarbon, or saturated heterocycloxy group, or
 —(C=O)—N(R³)(R⁴), or
 —(C=O)—OR⁵,
R³ and R⁴ are the same or different, and each represents:
 hydrogen or
 $C_{1-6}$ alkyl optionally substituted with at least one of halogen, hydroxyl, cyano, nitro, alkyl, halogenoalkyl, cycloalkyl, cycloalkyl-alkyl, aralkyl, alkenyl, alkynyl, alkoxy, halogenoalkoxy, cycloalkoxy, cycloalkyl-alkoxy, aralkyloxy, alkylthio, cycloalkyl-alkylthio, amino, mono- or di-alkylamino, cycloalkyl-alkylamino, acyl, acyloxy, oxo, carboxyl, alkoxycarbonyl, aralkyloxycarbonyl, carbamoyl, saturated or unsaturated heterocyclic group, aromatic hydrocarbon, or saturated heterocycloxy group;

or $R^3$ and $R^4$, taken together with a nitrogen atom to which $R^3$ and $R^4$ are attached, may form a saturated heterocyclic group; and $R^5$ represents:

hydrogen or $C_{1-6}$ alkyl optionally substituted with at least one of halogen, hydroxyl, cyano, nitro, alkyl, halogenoalkyl, cycloalkyl, cycloalkyl-alkyl, aralkyl, alkenyl, alkynyl, alkoxy, halogenoalkoxy, cycloalkoxy, cycloalkyl-alkoxy, aralkyloxy, alkylthio, cycloalkyl-alkylthio, amino, mono- or di-alkylamino, cycloalkyl-alkylamino, acyl, acyloxy, oxo, carboxyl, alkoxycarbonyl, aralkyloxycarbonyl, carbamoyl, saturated or unsaturated heterocyclic group, aromatic hydrocarbon, or saturated heterocycloxy group or Aralkyl wherein said carbamoyl group is selected from $CONH_2$, (mono- or di-alkyl)carbamoyl, (mono- or di-aryl)carbamoyl, (N-alkyl-N-aryl)carbamoyl, pyrrolidinocarbamoyl, piperidinocarbamoyl, piperazinocarbamoyl, or morpholinocarbamoyl.

* * * * *